United States Patent [19]

Watanabe et al.

[11] Patent Number: 4,647,656

[45] Date of Patent: Mar. 3, 1987

[54] AMINOGLYCOSIDE COMPOUNDS

[75] Inventors: Isamu Watanabe; Kazuhiro Kamiya, both of Higashimurayama; Takahiro Torii, Chofu; Toshihito Mori, Higashimurayama, all of Japan

[73] Assignee: Kowa Company, Ltd., Nagoya, Japan

[21] Appl. No.: 640,593

[22] Filed: Aug. 14, 1984

[30] Foreign Application Priority Data

Aug. 18, 1983 [JP] Japan ................... 58-149656

[51] Int. Cl.$^4$ ......................................... C07H 15/224
[52] U.S. Cl. ................... 536/16.1; 536/16.8; 530/322
[58] Field of Search ............... 260/112.5 R; 536/16.1, 536/16.8; 530/322

[56] References Cited

U.S. PATENT DOCUMENTS

| | | | |
|---|---|---|---|
| 4,250,304 | 2/1981 | Martin et al. | 536/16.1 |
| 4,382,926 | 5/1983 | Umezawa et al. | 536/16.1 |
| 4,418,193 | 11/1983 | McAlpine et al. | 536/16.1 |
| 4,431,799 | 2/1984 | Tadanier et al. | 536/16.1 |
| 4,479,943 | 10/1984 | Umezawa et al. | 536/16.1 |
| 4,487,924 | 12/1984 | Watanabe et al. | 536/16.1 |
| 4,504,472 | 3/1985 | Takaya et al. | 536/16.1 |
| 4,515,942 | 5/1985 | Iwasaki et al. | 536/16.1 |

Primary Examiner—Johnnie R. Brown
Attorney, Agent, or Firm—Wenderoth, Lind & Ponack

[57] ABSTRACT

An aminoglycoside compound represented by the following formula (1)

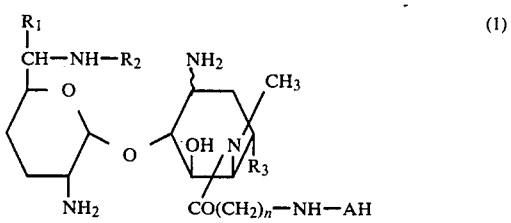

(1)

wherein
$R_1$ and $R_2$ are different from each other and each represents a hydrogen atom or a methyl group,
$R_3$ represents a hydrogen atom, a hydroxyl group or a methoxy group,
A represents a residue of a $C_2$–$C_{11}$ amino acid or a residue of a dipeptide composed of two said amino acids which are identical or different, and n represents 1 or 2;

and its acid addition salt; and a process for the production thereof.

3 Claims, No Drawings

AMINOGLYCOSIDE COMPOUNDS

This invention relates to aminoglycoside compounds and their acid addition salts which have not been described in the literature and are useful as antibiotics or as synthetic intermediates of antibiotics. The invention also relates to processes for producing these aminoglycoside compounds and their acid addition salts.

More specifically, this invention pertains to aminoglycoside compounds represented by the following formula (1)

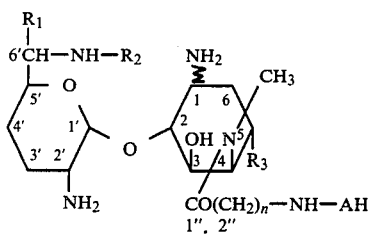

wherein
$R_1$ and $R_2$ are different from each other and each represents a hydrogen atom or a methyl group,
$R_3$ represents a hydrogen atom, a hydroxyl group or a methoxy group,
A represents a residue of a $C_2$–$C_{11}$ amino acid or a residue of a dipeptide composed of two said amino acids which are identical or different, and n represents 1 or 2;
and their acid addition salts. The invention also pertains to processes for producing the compounds of formula (1) and their acid addition salts.

Compounds represented by the following formulae (2) and (7) have been known previously.

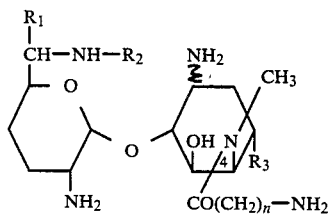

wherein $R_1$, $R_2$, $R_3$ and n are as defined above.

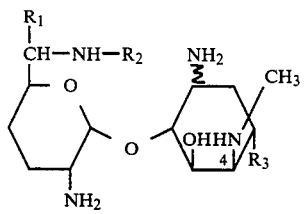

wherein $R_1$, $R_2$ and $R_3$ are as defined above.

These compounds represented by formulae (2) and (7) are known as KA-6606 substance obtained as a metabolite of a known *Saccharopolyspora hirsuta* KC-6606 strain (for example, ATCC 20501) and KA-7038 substance obtained as a metabolite of a known Streptomyces sp. KC-7038 strain (for example, ATCC 31530), and 4-N-glycyl derivatives, 5-de-O-methyl derivatives and 5-demethoxy derivatives of these known substances. They are described in detail, for example, in U.S. Pat. Nos. 4,206,206, 4,255,421, 4,312,858, 4,328,307, 4,329,426, 4,353,893 and 4,389,486, and Japanese Laid-Open Patent Publications Nos. 111497/1980 and 164695/1980.

The present inventors have undertaken works on the development of new antibiotics derived from the aforesaid KA-6606 substance and KA-7038 substance. Consequently, they have found that the compounds of formula (1) not described in the literature and their acid addition salts exist stably; and succeeded in synthesizing these compounds. It has also been found that the compounds of formula (1) and their acid addition salts are useful as antibiotics and also as synthetic intermediates of other antibiotics.

It is an object of this invention therefore to provide novel aminoglycoside compounds of formula (1) and their acid addition salts.

Another object of this invention is to provide processes for producing these compounds.

The above and other objects and advantages of this invention will become more apparent from the following description.

The novel aminoglycoside compounds of this invention are represented by the following formula (1).

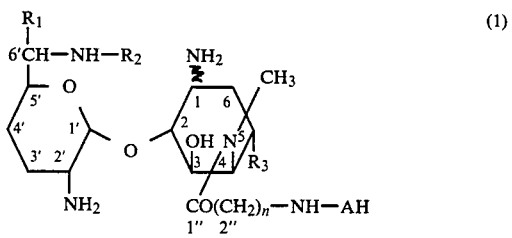

wherein
$R_1$ and $R_2$ are different from each other and each represents a hydrogen atom or a methyl group,
$R_3$ represents a hydrogen atom, a hydroxyl group or a methoxy group,
A represents a residue of a $C_2$–$C_{11}$ amino acid or a residue of a dipeptide composed of two said amino acids which are identical or different, and
n represents 1 or 2.

In the above formula (1), examples of preferred groups A are residues of natural alpha-amino acids having 2 to 11 carbon atoms or residues of dipeptides composed of two such alpha-amino acids which are identical or different. Specific examples of the groups A are residues of glycine, alanine, beta-alanine, valine, leucine, isoleucine, serine, threonine, aspartic acid, glutamic acid, asparagine, glutamine, cystine, cysteine, lysine, betalysine, ornithine, arginine, histidine, phenylalanine, tyrosine, tryptophan, proline and methionine, and residues of dipeptides composed of two such amino acids which are identical or different.

The acid addition salts of the compounds of formula (1) are preferably their pharmaceutically acceptable acid addition salts. Examples of the acid addition salts include their inorganic acid salts such as sulfates, hydrochlorides, hydrobromides, hydroiodides, phosphates, carbonates and nitrates, and their organic acid salts such as acetates, fumarates, malates, citrates, mandelates and succinates.

Examples of the aminoglycoside compounds of formula (1) and their acid addition salts in accordance with this invention are shown below. The KA-6606 substance and KA-7038 substances in the following examples have the structural formulae given hereinafter as starting compounds.

(1) 2″-N-L-Lysyl-5-de-O-methyl-KA-6606I compound and its acid addition salts.
(2) 2″-N-L-Tyrosyl-5-de-O-methyl-KA 6606I compound and its acid addition salts.
(3) 2″-N-L-Arginyl-5-de-O-methyl-KA-6606I compound and its acid addition salts.
(4) 2″-N-L-Aspartyl-5-de-O-methyl-KA-6606I compound and its acid addition salts.
(5) 2″-N-L-Glutamyl-5-de-O-methyl-KA-6606I compound and its acid addition salts.
(6) 2″-N-L-Glycyl-5-de-O-methyl-KA-6606I compound and its acid addition salts.
(7) 2″-N-L-Alanyl-5-de-O-methyl-KA-6606I compound and its acid addition salts.
(8) 2″-N-beta-Alanyl-5-de-O-methyl-KA-6606I compound and its acid addition salts.
(9) 2″-N-(L-Aspartyl-L-lysyl)-5-de-O-methyl-KA-6606I compound and its acid addition salts.
(10) 2″-N-(L-Aspartyl-L-tyrosyl)-5-de-O-methyl-KA-6606I compound and its acid addition salts.
(11) 2″-N-(beta-O-Methyl-L-aspartyl-L-tyrosyl)-5-de-O-methyl-KA-6606I compound and its acid addition salts.
(12) 2″-N-(beta-O-Methyl-L-aspartyl-L-lysyl)-5-de-O-methyl-KA-6606I compound and its acid addition salts.
(13) 2″-N-L-Aspartyl-5-demethoxy-KA-6606I compound and its acid addition salts.
(14) 2″-N-L-Glutamyl-KA-7038I compound and its acid addition salts.
(15) 4-N-(Glycyl-beta-alanyl)-5-de-O-methyl-KA-6606II compound and its acid addition salts.
(16) 2″-N-L-Phenylalanyl-5-de-O-methyl-KA-6606I compound and its acid addition salts.
(17) 2″-N-L-Seryl-5-de-O-methyl-KA-6606I compound and its acid addition salts.
(18) 2″-N-L-Tryptophyl-5-de-O-methyl-KA-6606I compound and its acid addition salts.
(19) 2″-N-L-Methionyl-5-de-O-methyl-KA-6606I compound and its acid addition salts.
(20) 2″-N-L-Prolyl-5-de-O-methyl-KA-6606I compound and its acid addition salts.
(21) 2″-N-(L-Glutamyl-L-glutamyl)-5-de-O-methyl-KA-6606I compound and its acid addition salts.
(22) 2″-N-(L-Leucyl-L-glycyl)-5-de-O-methyl-KA-6606I compound and its acid addition salts.
(23) 2″-N-L-Tryptophyl-5-demethoxy-KA-6606I compound and its acid addition salts.
(24) 2″-N-L-Tryptophyl-KA-6606I compound and its acid addition salts.
(25) 2″-N-L-Isoleucyl-5-de-O-methyl-KA-6606I compound and its acid addition salts.
(26) 2″-N-L-Histidyl-5-de-O-methyl-KA-6606I compound and its acid additon salts.
(27) 2″-N-D-Tryptophyl-5-de-O-methyl-KA-6606I compound and its acid addition salts.
(28) 2″-N-(L-Glutamyl-beta-alanyl)-5-de-O-methyl-KA-6606II compound and its acid addition salts.
(29) 4-N-(L-Tryptophyl-beta-alanyl)-5-de-O-methyl-KA-6606II compound and its acid addition salts.

Industrially, the novel aminoglycoside compounds of formula (1) and their acid addition salts can be produced easily by any of the following processes (i) to (iii).

Process (i)

A compound represented by the following formula (2)

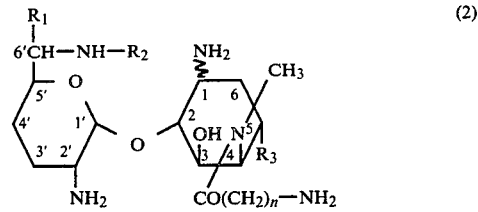

wherein $R_1$ and $R_2$ are different from each other and each represents a hydrogen atom or a methyl group, $R_3$ represents a hydrogen atom, a hydroxyl group or a methoxy group, and n represents 1 or 2, or a compound resulting from protecting amino groups of the compound of formula (2) excepting the 4-position side-chain amino group is reacted with a compound represented by the following formula (3)

$$HO-A-H \qquad (3)$$

wherein A represents a residue of an amino acid having 2 to 11 carbon atoms or a residue of a dipeptide composed of two said amino acids, or a compound resulting from protecting the functional groups of the compound of formula (3) excepting one carboxyl group, or a compound resulting from converting said one carboxyl group of the compound of formula (3) into its reactive derivative. As required, the resulting product of formula (1) is contacted with an acid to convert it into its acid addition salt.

Process (ii)

The compound of formula (2) or the compound resulting from protecting the amino groups of the compound of formula (2) excepting the 4-position side-chain amino group is reacted with a compound represented by the following formula (4)

$$HO-A'-H \qquad (4)$$

wherein A' represents a residue of an amino acid having 2 to 11 carbon atoms, or a compound resulting from protecting the functional groups of the compound of formula (4) excepting one carboxyl group, or a compound resulting from converting said one carboxyl group of the compound of formula (4) into its reactive derivative to form a compound represented by the following formula (5)

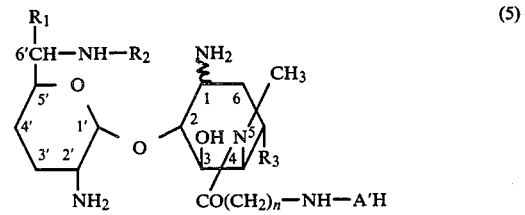

wherein $R_1$, $R_2$, $R_3$ and A' are as defined above. When the amino group in A' is protected, the protective group is split off. Thus, the compound of formula (5) or its deprotected compound is reacted with a compound represented by the following formula (6)

HO—A″—H                                              (6)

wherein A″ may be identical with or different from A′, and represents a residue of an amino acid having 2 to 11 carbon atoms, a compound resulting from protecting the functional groups of the compound of formula (6) excepting one carboxyl group, or a compound resulting from converting said one carboxyl group of the compound of formula (6) into its reactive derivative. As required, the reaction product of formula (1) obtained is contacted with an acid to convert it into its acid addition salt.

Process (iii)

A compound represented by the following formula (7)

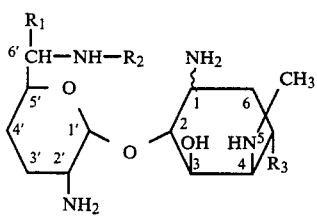

wherein R₁, R₂ and R₃ are as defined above, or a compound resulting from protecting the amino groups of the compound of formula (7) excepting the 4-position amino group is reacted with a compound of the following formula (8)

HOOC—(CH₂)ₙ—NH—AH                    (8)

wherein A and n are as defined, or a compound resulting from protecting the functional groups of the compound of formula (8) excepting HOOC—, or a compound resulting from converting the HOOC— of the compound of formula (8) into its reactive derivative. As required, the resulting reaction product (1) is contacted with an acid to convert it into its acid addition salt.

In the aforesaid processes for producing the amino glycosides compounds of formula (1) and their acid addition salts in accordance with this invention, the starting compounds of formulae (2) and (7) and processes for their production are known, and can be used in this invention. Examples of the known KA-6606 substance and KA-7038 substance are those of the following structural formulae.

Starting compounds of formula (2)

KA-6606I (4-N—glycyl-KA-6606II)

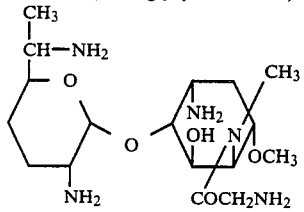

4-N—glycyl-KA-6606VI

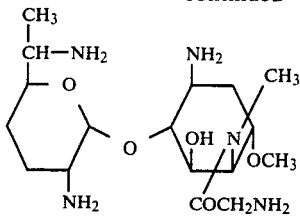

KA-7038I (4-N—glycyl-KA-7038III)

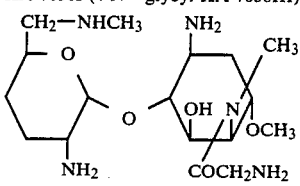

5-de-O-methyl compound and 5-demethoxy compound derived from the above compounds.

Starting compounds of formula (7)

KA-6606II

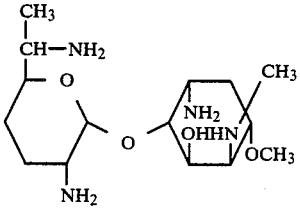

KA-6606VI

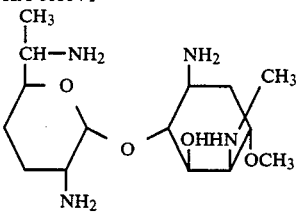

KA-7038III

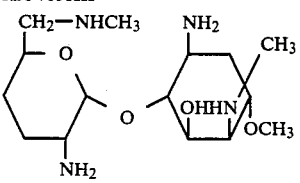

5-de-O-methyl compound and 5-demethoxy compound derived from the above compounds.

Examples of the compound of formula (3) in process (i) and the compounds (4) and (6) in process (ii) include amino acids such as glycine, alanine, beta-alanine, valine, leucine, isoleucine, serine, threonine, aspartic acid, glutamic acid, asparagine, glutamine, cystine, cysteine, lysine, beta-lysine, ornithine, arginine, histidine, phenylalanine, tyrosine, tryptophan, proline and methionine, and dipeptides obtained by condensing two of these amino acids which are identical or different. Examples of the compound of formula (8) in process (iii) are those in which A in formula (8) represents residues of the above-exemplified amino acids or dipeptides.

In the production of the compounds of formula (1) in accordance with this invention by process (i) or (iii), the reaction is carried out preferably by using the compound obtained by protecting the amino groups of the compound of formula (2) or (7) excepting the 4-position side-chain amino group, such as the amino groups at the 1-, 2'-and 6'-positions, with suitable protective groups and the compounds of formula (3) in which the functional groups excepting one carboxyl groups, for example an amino group and another carboxyl group, are protected with suitable protective groups or the protected compound of formula (3) in which the aforesaid one carboxyl group is converted into its reactive derivative, or the compound of formula (8) in which the functional groups other than HOOC—, such as an amino group and another carboxyl group, are protected with suitable protective groups, or the protected compound of formula (8) in which the HOOC— is converted into its reactive derivative. After the reaction, the compound of formula (1) having no protective group can be easily obtained by splitting off the protective groups by a technique known per se.

The compound of formula (1) in which A is a residue of a dipeptide can also be produced by process (ii). According to one preferred embodiment, the compound of formula (2) in which the amino groups other than the 4-position side-chain amino group are protected is reacted with the compound of formula (4) in which the functional groups other than one carboxyl group, such as an amino group and another carboxyl group, are protected with suitable protective groups or the protected compound of formula (4) in which the aforesaid one carboxyl group is converted into its reactive derivative. The protective groups for one amino group in A' of the resulting compound of formula (5) are split off and then reacted with the compound of formula (6) in which the functional groups other than one carboxyl group, for example an amino group and another carboxyl group, are protected with suitable protective groups. After the reaction, the compound of formula (1) having no protective group can be easily obtained by splitting off the protective groups by a technique known per se. In performing this preferred embodiment, it is desirable to protect one amino group of the compound of formula (4) with a protective group which can be split off under different conditions from those under which the protective groups protecting the amino groups of the compound of formula (2) can be split off. This is for the purpose of preventing splitting off of the protective groups for the compound of formula (2) at the time of splitting off the protective groups for the amino groups in A' of the compound of formula (5).

Examples of the reactive derivatives obtained by conversion of the carboxyl groups of the compounds of formulae (3), (4), (6) and (8) include acid chlorides, acid azides, acid anhydrides, mixed acid anhydrides, active esters, enol ethers and active amides.

In the process of this invention, the compound of formula (2) in which the amino groups at the 1-, 2'- and 6'-positions are protected can also be obtained by protecting the amino groups at the 1-, 2'- and 6'-positions of the compound of formula (7), and then acylating the amino group at the 4-position. The compond of formula (2) in which the amino groups at the 1-, 2'- and 6'-positions are protected can be produced from the compound of formula (7) by utilizing the following methods.

First, the amino groups of the compound of formula (7) are protected in a customary manner, for example with benzyloxycarbonyl groups. Generally, this results in simultaneous protection of the amino groups at the 1-, 4-, 2'- and 6'-positions. But the amino groups at the 1-, 2'-and 6'-positions can be selectively protected by properly selecting the protective group introducing agent in the presence of a divalent metal such as nickel acetate, cobalt acetate or zinc acetate. The preferred introducing agent is, for example, an active ester of a carboxylic acid, preferably its substituted phenyl ester, N-oxysuccinimide ester or N-oxyphthalimide ester. When the methylamino group at the 4-position is simultaneously protected, the methylamino group at the 4-position can be easily rendered free by forming a cyclic carbamate between the hydroxyl group at the 3-position and the methylamino group at the 4-position and then hydrolyzing it. Alternatively, by reacting the tetra-N-protected compound of the compound of formula (7) with an alkali in a water-containing solvent, the methylamino group at the 4-position can be directly rendered free.

When the resulting compound of formula (7) in which the amino groups at the 1-, 2'- and 6'-positions are protected is acylated with a compound represented by the general formula $$HOOC-(CH_2)_n-NH_2 \qquad (9)$$

wherein n is as defined hereinabove, a compound of formula (2) in which the amino groups at the 1-, 2'- and 6'-positions are protected can be obtained. The acylation is carried out preferably by using the active derivative at the carboxyl group of the compounds of formula (9) having protected amino groups, particularly its succinimide ester. Preferred protective groups for the amino groups are those which can be split off under different conditions from those under which other protective groups such as benzyloxycarbonyl groups are split off. Examples are a diphenylphosphinothioyl group, a p-methoxybenzyloxycarbonyl group and a t-butoxycarbonyl group. When subsequent to the acylation, the protective group for the amino group at the 4-position side chain is split off, for example by acid treatment, the 1,2',6'-tris-N-protected compound of formula (2) is obtained.

The compound of formula (2) in which $R_3$ is a hydroxyl group can be produced from the starting compound of formula (7) having a methylamino group at the 4-position by de-O-methylating it by the method described in U.S. Pat. No. 4,255,421. The compound of formula (2) in which $R_3$ is a hydrogen atom can be obtained by dehydroxylating the compound of formula (2) in which $R_3$ is a hydroxyl group produced by the above method, by the method described in U.S. Pat. No. 4,353,893.

Preferably, the de-O-methylation reaction ($R_3$: OCH$_3$→OH) is carried out before the reaction of protecting the amino groups at the 1-, 2'- and 6'-positions. If desired, the de-O-methylation can be carried out after protecting the amino groups. By acylating the resulting compound with the compound of formula (9) and splitting off the protective group for the amino group in the 4-position side chain, the desired 1,2',6'-tri-N-protected compound of formula (2) ($R_3$=OH) can be obtained. The aforesaid dehydroxylation reaction ($R_3$:OH; H) is carried out generally after the amino groups at the 1-, 2'-, 6'- and 4-positions and the hydroxyl group at the 3-position are protected. After the end of this reaction, the protective groups for the methylamino group at the 4-position and the hydroxyl group at the 3-position are split off and the 4-position is acylated. Subsequent splitting off of the protective group for the 4-position side-chain amino group gives the desired 1,2',6'-tris-N-protected compound of formula (2) ($R_3$=H).

The protective groups for the amino groups of the compounds of formulae (3), (6) and (8) may preferably be split off under the same conditions as those under which the protective groups for the compound of formula (2) and (7) split off. Preferably, they are the same as the protective groups for the compound of formula (2) and (7).

The protective groups for the amino groups of the compound of formula (4) used in process (ii) are preferably those which can be split off under conditions different from those under which the protective groups for the amino groups at the 1-, 2'- and 6'-positions of the compound of formula (2) are split off. Specifically, it is possible, for example, (a) to protect the amino groups of the compound of formula (4) with benzyloxycarbonyl groups and the amino groups of the compound of formula (2) with t-butoxycarbonyl groups, (b) to protect the amino groups of the compound of formula (4) with p-methoxybenzyloxycarbonyl groups and the amino groups of the compound of formula (2) with benzyloxycarbonyl groups, or (c) to protect the amino groups of the compound of formula (4) with t-butoxycarbonyl groups and the amino groups of the compounds of formula (2) with benzyloxycarbonyl groups. The protective groups for the functional groups of the compounds of formula (3), (4), (6) or (8) other than the amino groups and one carboxyl group, for example, another carboxyl group and a guanidino group, are preferably those which can be split off at the same time as the protective groups for the amino groups. For example, a benzyl ester residue is preferred for the carboxyl group, and a nitro group or a benzyloxycarbonyl group, for the guanidino group. These protective groups can be split off by a catalytic reducing method.

The reaction of the comound of formula (2), (5) or (7) with the compound of formula (3), (4), (6) or (8) may be carried out by the following methods used in the field of peptide syntheses.

(A) The two compounds are reacted in the presence of a dehydrating agent or a condensing agent. An example of the dehydrating agent is N,N'-dicyclohexyl carbodiimide, and examples of the condensing agent are chloroformates and chlorophosphites.

(B) The compound of formula (2), (5) or (7) and the acid reactive derivatives of the compound of formula (3), (4), (6) or (8) are reacted. Examples of the acid reactive derivatives include acid chlorides, acid azides, acid anhydrides, mixed acid anhydrides, active esters and active amides, particularly active esters such as p-nitrophenyl esters, cyanomethyl esters, N-hydroxysuccinimide esters and N-hydroxyphthalimide esters.

When the present reaction is carried out, for example, by using the method (A), the compound of formula (2), (5) or (7) in which the amino group at the 4-position or the side chain at the 4-position is free is reacted with 1 to 5 times its amount of the free carboxylic acid of formula (3) (4), (6) or (8) in a solvent in the presence of a dehydrating agent or a condensing agent at a temperature of 0° to 100° C. for 1 to 40 hours. Examples of the solvent that can be used include tetrahydrofuran, acetonitrile, dichloromethane, pyridine, dioxane, and dimethylformamide.

When the method (B) is to be used, the reactive derivatives, for example active esters, of the compounds of formula (3), (4), (6) or (8) and the compound of formula (2), (5) or (7) are used nearly in equivalent weights, and reacted in the same solvent as exemplified above in the presence or absence of a base at a temperature of 0° to 100° C. for a period of 1 to 40 hours. Examples of the base are triethylamine, pyridine and diazabicycloundecene.

When the protective groups of the resulting compound of formula (1) in which the amino groups and other functional groups are protected are split off, the free compound of formula (1) is obtained. Ordinary methods can be applied to the elimination of the protective groups, but the use of a catalytic reducing method and an acid-catalyzed cleavage method is preferred.

Palladium, platinum, Raney nickel, rhodium, ruthenium and nickel can be exemplified as a catalyst for the catalytic reduction. The catalytic reduction may be carried out in the same solvent as exemplified above. This reaction can be carried out, for example, at a hydrogen pressure of 1 to 5 atmospheres and a temperature of 0° to 100° C. for 0.1 to 10 hours.

Acid-catalyzed cleavage can be carried out by contacting the compound of formula (1) in which the amino groups and other functional groups are protected with an acid in a solvent. Examples of the acid are hydrochloric acid, hydrobromic acid and hydrofluoric acid. The solvent may be acetic acid, methanol, ethanol, dioxane, water, etc. The reaction can be carried out, for example, at 0° to 100° C. for 1 to 10 hours.

The desired compound of formula (1) and the compound of formula (1) in which the amino groups are protected can be isolated and purified by conventional methods, preferably by column chromatography. It is preferred to use cation exchange resins such as CM-Sephadex, Amberlite IRC-50, IRC-84 and CG-50, carboxymethyl cellulose, silica gel and cellulose as an adsorbent. The column may be developed with a developing solvent, for example an aqueous alkaline solution such as aqueous ammonia and an aqueous solution of ammonium formate or an organic solvent such as chloroform and methanol by a concentration gradient method or a concentration stepwise method. Active fractions are collected from the eluates, and lyophilized to give the desired compound as a pure product.

The compound of formula (1) can be converted to acid addition salts by contacting it with acids. Examples of the acids are inorganic acids such as sulfuric acid, hydrochloric acid, hydrobromic acid, hydroiodic acid, phosphoric acid, carbonic acid and nitric acid, and organic acids such as fumaric acid, malic acid, citric acid, mandelic acid and succinic acid. The reaction of forming the acid addition salt is carried out by adding the acid in an amount required for neutralization to an aqueous solution of the compound of formula (1), and lyophilizing the resulting product.

The aminoglycoside compounds and their acid addition salts in accordance with this invention are useful as antibiotics or as synthetic intermediates for other antibiotics.

Their antibacterial activity is shown below.

Test for Antibacterial activity

Each of the test compounds shown in the following table was dissolved in a concentration of 200 mcg/ml in a homogenate of a 10% physiological saline solution of an organ of a rat, and incubated at 37° C. for 2 hours. An enzymatic reaction was stopped by adding an equal amount of ethanol. The antibacterial activity of the test compound before incubation was compared with that after incubation.

The antibacterial activity was measured by a paper disk having a diameter of 8 mm using *Bacillus subtilis* ATCC 6633 as a test organism, and shown by the diameter of the resulting inhibitory zone. The results are tabulated below. In view of these results, the compounds of formula (1) and their acid addition salts are expected to have excellent antibacterial activity in vivo.

| Test compound No. | Diameter of the inhibitory zone (mm) | |
|---|---|---|
| | Before incubation | After incubation |
| 1 | 17 | 26* |
| 2 | 16.5 | 24* |
| 3 | 14.5 | 22* |
| 4 | 15 | 15* |
| 5 | 13 | 19* |
| 7 | 21 | 22* |
| 10 | 12 | 16* |
| 11 | 13 | 21* |
| 12 | 14 | 24* |
| 13 | 14 | 15* |
| 14 | 14 | 18 |
| 16 | 24 | 25* |
| 17 | 15 | 22.5 |
| 18 | 15 | 19 |
| 19 | 13 | 19 |
| 20 | 19 | 26 |
| 21 | 16 | 17 |
| 26 | 20 | 23 |
| 27 | 13 | 22.5 |
| 29 | 13 | 20* |

The asterisks show that the incubation was carried out in a liver homogenate. Otherwise, the incubation was carried out in an equal amount mixture of a liver homogenate and a kidney homogenate.

The compounds of formula (1) and their acid addition salts can be formed into pharmaceutical compositions of various known forms by methods known per se. Examples of forms are capsules, tablets, pills, powders, granules, particles, solutions, suspensions, syrups, elixirs and suppositories.

According to this invention, there can be provided a pharmaceutical composition comprising an antibacterially effective amount of the compound of formula (1) or its acid addition salt and a pharmaceutically acceptable diluent or carrier. Examples of such diluents or carriers include liquid diluents such as distilled water for injection, physiological isotonic solution, alcohols, propylene glycol, polyethylene glycol, vegetable oils (ie., olive oil), and organic esters such as ethyl oleate, and solid carriers such as lactose, starch, white sugar, glucose, crystalline cellulose, calcium carbonate, kaolin, D-mannitol, magnesium metasilicate aluminate, calcium sulfate, calcium phosphate, bentonite, cacao butter and suppository waxes.

The pharmaceutical composition can be administered through various routes, such as intramuscular, intravenous, subcutaneous, intrarectal and oral. The dose of the compound of formula (1) or its acid addition salt may, for example, be about 0.1 to about 100 mg/kg/day.

The following examples illustrate the compounds of this invention and processes for their production in greater detail.

REFERENTIAL EXAMPLE 1

Production of 1,2',6'-tris-N-benzyloxycarbonyl-5-de-O-methyl-KA-6606I (A) Five hundred mg of 1,2',6'-tris-N-benzyloxycarbonyl-5-de-O-methyl-KA-6606 II was dissolved in 15 ml of dioxane, and 450 mg of the N-hydroxysuccinimide ester of N-diphenylphosphinothioylglycine and 0.5 ml of triethylamine were added. The mixture was left to stand overnight at room temperature. The reaction mixture was concentrated to dryness. The residue was dissolved in chloroform, washed with water and dried. The solvent was evaporated. The residue was charged on a silica gel column and eluted with chloroform/methanol (40:1). Fractions containing the desired final substance were collected and treated in a customary manner to give 440 mg of 1,2',6'-tris-N-benzyloxycarbonyl-2''-N-diphenylphosphinothioyl- 5-de-O-methyl-KA-6606I as a colorless solid.

Specific rotation: $[\alpha]_D^{25}+38°$ (c1, CHCl$_3$).

IR value: $\nu_{max}^{CHCl_3}$ cm$^{-1}$ 1640 (amide I).

$^1$H-NMR value: $\delta$CDCl$_3$ ppm 1.06 (3H, d, J=7.0 Hz, C—CH$_3$), 2.90 (3H, s, N—CH$_3$), 7.3–7.4 (25H, m, aromatic H).

Elemental analysis for C$_{52}$H$_{60}$N$_5$O$_{11}$PS:

| | C | H | N | P | S |
|---|---|---|---|---|---|
| Calculated (%) | 62.83 | 6.08 | 7.05 | 3.12 | 3.22 |
| Found (%) | 62.57 | 6.36 | 7.33 | 2.90 | 3.54 |

(B) The resulting 4-N-protected glycyl compound (320 mg) was dissolved in 9 ml of a mixture of tetrahydrofuran and concentrated hydrochloric acid (5:1), and left to stand at room temperature for 24 hours. Aqueous ammonia was added to the reaction mixture to adjust its pH to 5, and tetrahydrofuran was evaporated. Water (10 ml) was added to the residue and it was then extracted with chloroform. The extract was washed with a 0.5N aqueous solution of sodium hydroxide and water, and the solvent was evaporated. The residue was charged on a silica gel column, and eluted with chloroform/methanol/concentrated aqueous ammonia(60:10:1), and treated in a customary manner to give 131 mg of 1,2',6'-tris-N-benzyloxycarbonyl-5-de-O-methyl-KA-6606I of the following structural formula as a colorless solid. In the formula, Z represents the group

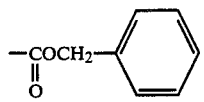

(the same applies hereinafter).

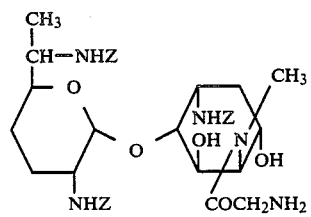

Specific rotation: $[\alpha]_D^{25}+51°$ (c1, CHCl$_3$).
IR value: $\nu_{max}^{CHCl_3}$ cm$^{-1}$ 1625 (amide I).
$^1$H-NMR value: $\delta$CDCl$_3$ ppm 1.03 (3H, d, J=7.0 Hz, C—CH$_3$), 2.88 (3H, s, N—CH$_3$).
Elemental analysis for C$_{40}$H$_{51}$N$_5$O$_{11}$:

|  | C | H | N |
|---|---|---|---|
| Calculated (%) | 61.76 | 6.61 | 9.00 |
| Found (%) | 61.58 | 6.32 | 9.27 |

REFERENTIAL EXAMPLE 2

Production of 1,2′,6′-tris-N-benzyloxycarbonyl-5-demethoxy-KA-6606I (A) One gram of 5-de-O-methyl-KA-6606II was dissolved in 10 ml of water, and 1.3 g of anhydrous sodium carbonate and 40 ml of methanol were added. With ice cooling, 2.6 ml of carbobenzyloxy chloride was added dropwise, and stirred for 3 hours under ice cooling. The reaction mixture was concentrated to dryness. Chloroform was added to the residue. The mixture was washed with water and dried, and the solvent was evaporated to give 2.6 g of colorless crystals. Recrystallization from benzene gave 1,4,2′,6′-tetrakis-N-benzyloxycarbonyl-5-de-O-methyl-KA-6606II as colorless needles having a melting point of 153° to 154° C.
Specific rotation: $[\alpha]_D^{23}+44°$ (c1, CHCl$_3$).
Elemental analysis for C$_{46}$H$_{54}$N$_4$O$_{12}$:

|  | C | H | N |
|---|---|---|---|
| Calculated (%) | 64.62 | 6.37 | 6.55 |
| Found (%) | 64.49 | 6.33 | 6.61 |

(B) The resulting N-protected compound (100 mg) was dissolved in 2 ml of dioxane, and 1.5 ml of a 0.1M aqueous solution of barium hydroxide. The mixture was stirred at 60° C. for 1 hour. Dry ice was added to the reaction mixture to neutralize it. The insoluble materials were separated by filtration, and the filtrate was concentrated to dryness. The residue was separated and purified by preparative thin-layer chromatography to give 68 mg of 1,2′,6′-tris-N-benzyloxycarbonyl-3-0:4-N-carbonyl-5-de-O-methyl-KA-6606II as a colorless solid.
Specific rotation: $[\alpha]_D^{23}+33°$ (c1, CHCl$_3$).
IR value: $\nu_{max}^{CHCl_3}$ cm$^{-1}$ 1760 (cyclic carbamate).
$^1$H-NMR value: $\delta$CDCl$_3$ ppm 1.07 (3H, d, J=6 Hz, C—CH$_3$), 2.87 (3H, s, N—CH$_3$).
Elemental analysis for C$_{39}$H$_{46}$N$_4$O$_{11}$:

|  | C | H | N |
|---|---|---|---|
| Calculated (%) | 62.72 | 6.21 | 7.50 |
| Found (%) | 62.48 | 6.10 | 7.28 |

(C) Two grams of the resulting N,O-protected compound was dissolved in 40 ml of dichloromethane, and 4 ml of pyridine and 1.6 ml of sulfuryl chloride were added at −10° C. The mixture was left to stand at −10° C. for 12 hours and then at 5° C. for 4 hours. The reaction mixture was poured into a mixture of 200 ml of chloroform and 200 ml of a saturated aqueous solution of sodium bicarbonate. The chloroform layer was separated, washed with a saturated aqueous solution of sodium bicarbonate and dried. The solvent was evaporated. The residue was dissolved in 40 ml of benzene, and heated at 70° C. for 3 hours. The solvent was evaporated. The residue was charged on a silica gel column, and eluted with chloroform-methanol (100:1) to give 1.3 g of 1,2′,6′-tris-N-benzyloxycarbonyl-3-0:4-N-carbonyl-5-chloro-5-demethoxy-KA-6606II as a colorless solid.
Specific rotation: $[\alpha]_D^{23}+24°$ (c2, CHCl$_3$).
IR value: $\nu_{max}^{CHCl_3}$ cm$^{-1}$ 1760 (cyclic carbamate).
$^1$H-NMR value: $\delta$CDCl$_3$ ppm 1.06 (3H, d, J=6 Hz, C—CH$_3$), 2.86 (3H, s, N—CH$_3$).
Elemental analysis for C$_{39}$H$_{45}$ClN$_4$D$_{10}$:

|  | C | H | N | Cl |
|---|---|---|---|---|
| Calculated (%) | 61.21 | 5.93 | 7.32 | 4.63 |
| Found (%) | 60.98 | 5.81 | 7.51 | 4.55 |

(D) The resulting 5-chloro compound (1.2 g) was dissolved in 24 ml of toluene, and 1.5 ml of tri-n-butylstannane was added. After the mixture was purged with nitrogen, 20 mg of azobisisobutyronitrile was added. The mixture was heated at 80° C. for 4 hours. The reaction mixture was concentrated to dryness. The residue was charged on a silica gel column, eluted with chloroform/methanol (100:1), and treated in a customary manner to give 1.13 g of 1,2′,6′-tris-N-benzyloxycarbonyl-3-0:4-N-carbonyl-5-demethoxy-KA-6606II as a colorless solid.
Specific rotation: $[\alpha]_D^{24}+3°$ (c2, CHCl$_3$).
IR value: $\nu_{max}^{CHCl_3}$ cm$^{-1}$ 1755 (cyclic carbamate).
$^1$H-NMR value: $\delta$CDCl$_3$ ppm 1.07 (3H, d, J=7 Hz, C—CH$_3$), 2.73 (3H, s, N—CH$_3$).
Elemental analysis for C$_{39}$H$_{46}$N$_4$O$_{10}$:

|  | C | H | N |
|---|---|---|---|
| Calculated (%) | 64.10 | 6.34 | 7.67 |
| Found (%) | 63.95 | 6.32 | 7.61 |

(E) The 5-demethoxy compound (1.14 g) was dissolved in 17 ml of dioxane, and 17 ml of a 0.45M aqueous solution of barium hydroxide. The mixture was heated at 60° C. for 16 hours with stirring. The reaction mixture was neutralized with carbon dioxide gas and concentrated to dryness. The residue was dissolved in chloroform, washed with water and dried. The solvent was then evaporated.
The residue was dissolved in 25 ml of dioxane, and 750 mg of the N-hydroxysuccinimide ester of N-diphenyl-phosphinothioylglycine and 0.8 ml of triethylamine were added. The mixture was left to stand overnight at room temperature. The reaction mixture was concentrated to dryness. The residue was dissolved in chloroform, washed with water and dried. The solvent was evaporated. The residue was charged on a silica gel column, eluted with chloroform/ethyl acetate (5:2), and treated in a customary manner to give 643 mg of 1,2′,6′-tris-N-benzyloxycarbonyl-5-demethoxy-2″-N-diphenyl-phosphinothioyl-KA-6606I as a colorless solid.
Specific rotation: $[\alpha]_D^{25}+53°$ (c0.5, CHCl$_3$).
IR value: $\nu_{Max}^{CHCl_3}$ cm$^{-1}$ 1640 (amide I).
$^1$H-NMR value: $\delta$CDCl$_3$ ppm 1.08 (3H, d, J=7.0 Hz, C—CH$_3$), 2.81 (3H, s, N—CH$_3$), 7.3–7.4 (3H, m, aromatic H).
Elemental analysis for C$_{52}$H$_{60}$N$_5$O$_{10}$PS:

| | C | H | N | P | S |
|---|---|---|---|---|---|
| Calculated (%) | 63.85 | 6.18 | 7.16 | 3.17 | 3.28 |
| Found (%) | 63.99 | 6.35 | 7.41 | 2.98 | 3.11 |

(F) The resulting 4-N-protected-glycyl compound (520 mg) was reacted and worked up in the same way as in Referential Example 1, (B) to give 190 mg of 1,2',6'-tris-N-benzylolxycarbonyl-5-demethoxy-KA-6606I of the following structural formula as a colorless solid.

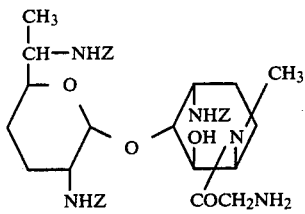

Specific rotation: $[\alpha]_D^{25} + 71°$ (c1, CHCl$_3$).
IR value: $\nu_{max}^{CHCl_3}$ cm$^{-1}$ 1625 (amide I).
$^1$H-NMR value: $\delta$CDCl$_3$ ppm 1.09 (3H, d, J=7.0 Hz, C—CH$_3$), 2.89 (3H, s, N—CH$_3$), 7.3 (15H, m, aromatic H).
Elemental analysis for C$_{40}$H$_{51}$N$_5$O$_{10}$:

| | C | H | N |
|---|---|---|---|
| Calculated (%) | 63.06 | 6.75 | 9.19 |
| Found (%) | 62.77 | 6.89 | 9.45 |

EXAMPLE 1

Production of 2''-N-L-lysyl-5-de-O-methyl-KA-6606I (A) The 1,2',6'-tris-N-benzyloxycarbonyl-5-de-O-methyl-KA-6606I obtained in Referential Example 1 (175 mg) was dissolved in 7.5 ml of dioxane, and 300 mg of the N-hydroxysuccinimide ester of bis-N-benzyloxycarbonyl-L-lysine and 0.2 ml of triethylamine were added. The mixture was left to stand overnight at room temperature.

The reaction mixture was concentrated to dryness. The residue was dissolved in chloroform, washed with water and dried, and then the solvent was evaporated. The residue was purified by silica gel column chromatography [solvent: chloroform/methanol (30:1)] to give 220 mg of 1,2',6'-tris-N-benzyloxycarbonyl-2''-N-(bis-N-benzyloxycarbonbyl-L-lysyl)-5-de-O-methyl-KA-6606I as a colorless solid.

Specific rotation: $[\alpha]_D^{22} + 24°$ (c2, CHCl$_3$).
$^1$H-NMR value: $\delta_{CDCl_3}^{TMS}$ ppm 1.04 (3H, d, J=6 Hz, C—CH$_3$), 2.93, 3.10 (total 3H, s, N—CH$_3$, rotational isomer).
Elemental analysis for C$_{62}$H$_{75}$N$_7$O$_{16}$:

| | C | H | N |
|---|---|---|---|
| Calculated (%) | 63.41 | 6.44 | 8.35 |
| Found (%) | 63.15 | 6.41 | 8.22 |

(B) The N-protected compounds obtained in (A) above (40 mg) was dissolved in 2.4 ml of 0.2N methanolic hydrochloric acid, and 40 mg of 5%-palladium on carbon was added. The compound was catalytically reduced at room temperature and atmospheric pressure. The catalyst was removed by filtration from the reaction mixture, and the filtrate was concentrated to dryness. The residue was then adsorbed on a column filled with 5 ml of CM-Sephadex C-25 (NH$_4^+$ type). The column was washed with water and eluted with 1.5N aqueous ammonia. Fractions whose ninhydrin reaction was positive were collected and lyophilized to give 12 mg of the desired compound as a white solid having the following structural formula.

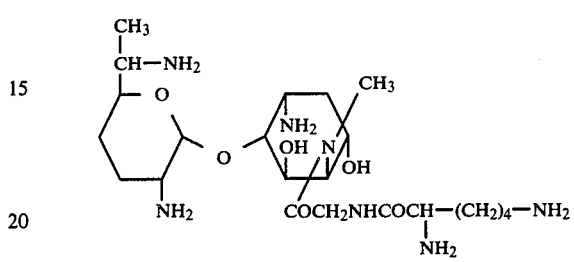

Specific rotation: $[\alpha]_D^{22} + 112°$ (c0.3, H$_2$O).
$^1$H-NMR value: $\delta_{D_2O}^{TMS}$ ppm 1.06 (3H, d, J=7 Hz, C—CH$_3$), 3.15 (3H, s, N—CH$_3$), 4.92 (1H, d, J=3 Hz, H-1').
Elemental analysis for C$_{22}$H$_{45}$N$_7$O$_6$·H$_2$O:

| | C | H | N |
|---|---|---|---|
| Calculated (%) | 50.65 | 9.08 | 18.80 |
| Found (%) | 50.62 | 8.83 | 18.44 |

EXAMPLE 2

Production of 2''-N-L-tyrosyl-5-de-O-methyl-KA-6606I (A) In the same way as in Example 1, (A), 175 mg of 1,2',6'-tris-N-benzyloxycarbonyl-5-de-O-methyl-KA-6606I and 158 mg of the N-hydroxysuccinimide ester of N-benzyloxycarbonyl-L-tyrosine were reacted, and the reaction product was purified by silica gel column chromatography [solvent: chloroform/methanol (30:1)] to give 205 mg of 1,2',6,'-tris-N-benzyloxycarbonyl-2''-N-(N-benzyloxycarbonyl-L-tyrosyl)-5-de-O-methyl-KA-6606I as a colorless solid.

Specific rotation: $[\alpha]_D^{22} + 40°$ (c2, CHCl$_3$).
$^1$H-NMR value: $\delta_{CDCl_3}^{TMS}$ ppm 1.02 (3H, d, J=6 Hz, C—CH$_3$), 2.84, 3.10 (total 3H, s, N—CH$_3$, rotational isomer), 6.73, 6.97 (each 2H, d, J=8 Hz, tyrosyl aromatic H).
Elemental analysis for C$_{57}$H$_{66}$N$_6$O$_{15}$:

| | C | H | N |
|---|---|---|---|
| Calculated (%) | 63.67 | 6.19 | 7.82 |
| Found (%) | 63.55 | 6.64 | 7.55 |

(B) The N-protected compound obtained in (A) above (40 mg) was catalytically reduced and purified in the same way as in Example 1, (B) to give 17 mg of the desired compound of the following structural formula as a colorless solid.

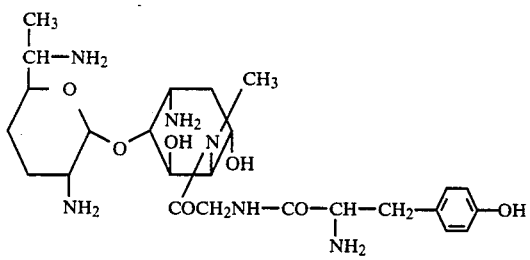

Specific rotation: $[\alpha]_D^{22} + 125°$ (c0.5, H$_2$O).

$^1$H-NMR value: $\delta_{D_2O}^{TMS}$ ppm 1.17 (3H, d, J=7 Hz, C—CH$_3$), 3.10 (3H, s, N—CH$_3$), 4.95 (1H, d, J=3.5 Hz, H-1′), 6.74, 7.06 (each 2H, d, J=8.5 Hz, tyrosyl aromatic H).

Elemental analysis for C$_{25}$H$_{42}$N$_6$O$_7$.2H$_2$O:

|  | C | H | N |
|---|---|---|---|
| Calculated (%) | 52.25 | 8.07 | 14.62 |
| Found (%) | 52.12 | 7.88 | 14.47 |

EXAMPLE 3

Production of
2″-N-L-arginyl-5-de-O-methyl-KA-6606I (A) Seventy milligrams of 1,2′,6′-tris-N-benzyloxycarbonyl-5-de-O-methyl-KA-6606I obtained in Referential Example 1 was dissolved in 2.6 ml of acetonitrile, and 27 mg of dicyclohexyl carbodiimide and 46 mg of N$^\alpha$-benzyloxycaronyl-N$^G$-nitro-L-arginine were added. The mixture was stirred overnight at room temperature. The insoluble materials were removed by filtration, and the filtrate was concentrated to dryness. The residue was purified by silica gel column chromatography [solvent: chloroform/methanol (15:1)] to give 46 mg of 1,2′,6′-tris-N-benzyloxycaronyl-2″-N-(N$^\alpha$-benzyloxycarbonyl-N$^G$-nitro-L-arginyl)-5-de-O-methyl-KA-6606I as a colorless solid.

Specific rotation: $[\alpha]_D^{20} + 36°$ (c1, CHCl$_3$).

$^1$H-NMR value: $\delta_{CDCl_3}^{TMS}$ ppm 1.01 (3H, d, J=6 Hz, C—CH$_3$), 2.91 (3H, s, N—CH$_3$).

Elemental analysis for C$_{54}$H$_{66}$N$_{10}$O$_{16}$:

|  | C | H | N |
|---|---|---|---|
| Calculated (%) | 58.26 | 6.16 | 12.58 |
| Found (%) | 57.87 | 6.22 | 12.45 |

(B) The N-protected compound obtained in (A) above (46 mg) was dissolved in 2 ml of 0.1N methanolic hydrochloric acid, and catalytically reduced by using 50 mg of 5%-palladium on carbon. The catalyst was removed by filtration, and the filtrate was concentrated. The residue was lyophilized to give 28 mg of the hydrochloride of the desired compound having the following structural formula as a colorless solid.

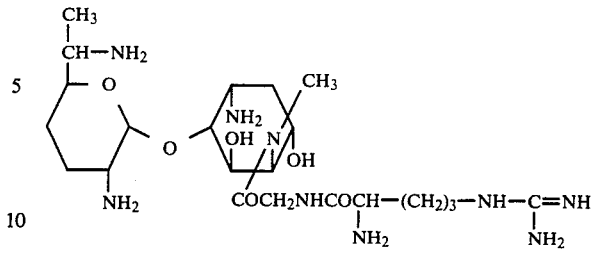

Specific rotation: $[\alpha]_D^{22} + 70°$ (c1, H$_2$O).

$^1$H-NMR value: $\delta_{D_2O}^{TMS}$ ppm 1.36 (3H, d, J=7 Hz, C—CH$_3$), 3.18 (3H, s, N—CH$_3$), 5.50 (1H, d, J=3.5 Hz, H-1′).

Elemental analysis for C$_{22}$H$_{45}$N$_9$O$_6$.6HCl.H$_2$O:

|  | C | H | N | |
|---|---|---|---|---|
| Calculated (%) | 34.38 | 6.95 | 16.41 | 27.68 |
| Found (%) | 33.97 | 7.03 | 16.28 | 28.03 |

EXAMPLE 4

Production of
2″-N-L-aspartyl-5-de-O-methyl-KA-6606I (A) In the same way as in Example 1, (A), 70 mg of 1,2′,6′-tris-N-benzyloxycarbonyl-5-de-O-methyl-KA-6606I obtained in Referential Example 1 and 55 mg of the N-hydroxysuccinimide ester of N-benzyloxycarbonyl-beta-O-benzyl-L-aspartic acid were reacted. The reaction product was purified by preparative thin-layer chromatography [carrier: silica gel; solvent: chloroform/methanol (15:2)] to give 78 mg of 1,2′,6′-tris-N-benzyloxycarbonyl-2″-N-(N-benzyloxycarbonyl-beta-O-benzyl-L-aspartyl)-5-de-O-methyl-KA-6606I as a colorless solid.

Specific rotation: $[\alpha]_D^{24} + 32°$ (c2, CHCl$_3$).

$^1$H-NMR value: $\delta_{CDCl_3}^{TMS}$ ppm 1.02 (3H, d, J=6 Hz, C—CH$_3$), 2.88, 3.04 (total 3H, s, N—CH$_3$, rotational isomer).

Elemental analysis for C$_{59}$H$_{68}$N$_6$O$_{16}$:

|  | C | H | N |
|---|---|---|---|
| Calculated (%) | 63.43 | 6.14 | 7.52 |
| Found (%) | 63.41 | 5.88 | 7.45 |

(B) The N,O-protected compound obtained in (A) above (75 mg) was reacted and worked up in the same way as in Example 3, (B) to give 39 mg of the hydrochloride of the desired compound as a colorless solid having the following structural formula

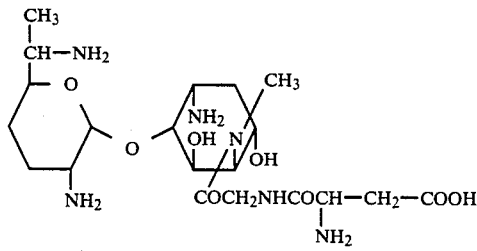

Specific rotation: $[\alpha]_D^{24} + 70°$ (c1, H$_2$O).

$^1$H-NMR value: $\delta_{D_2O}^{TMS}$ ppm 1.36 (3H, d, J=7 Hz, C—CH$_3$), 3.12 (2H, m, —CH$_2$—COOH), 3.17 (3H, s, N—CH$_3$), 5.48 (1H, d, J=3.5 Hz, H-1').

EXAMPLE 5

Production of 2''-N-L-glutamyl-5-de-O-methyl-KA-6606I (A) In the same way as in Example 1, (A), 175 mg of 1,2',6'-tris-N-benzyloxycarbonyl-5-de-O-methyl-KA-6606I obtained in Referential Example 1 and 150 mg of the N-hydroxysuccinimide ester of N-benzyloxycarbonyl-gamma-O-benzyl-L-glutamic acid were reacted, and the reaction product was purified by silica gel column chromatography [solvent: chloroform/methanol (40:1)] to give 130 mg of 1,2',6'-tris-N-benzyloxycarbonyl-2''-N-(N-benzyloxycarbonyl-gamma-O-benzyl-L-glutamyl)-5-de-O-methyl-KA-6606I as a colorless solid.

Specific rotation: $[\alpha]_D^{24}+29°$ (c2, CHCl$_3$).

$^1$H-NMR value: $\delta_{CDCl_3}^{TMS}$ ppm 1.05 (3H, d, J=6.5 Hz, C—CH$_3$), 2.90, 3.04 (total 3H, s, N—CH$_3$, rotational isomer).

Elemental analysis for C$_{60}$H$_{70}$N$_6$O$_{16}$:

|  | C | H | N |
|---|---|---|---|
| Calculated (%) | 63.70 | 6.24 | 7.43 |
| Found (%) | 63.81 | 6.03 | 6.98 |

(B) The N,O-protected compound obtained in (A) above (130 mg) was reacted and worked up in the same way as in Example 3, (B) to give 72 mg of the hydrochloride of the desired compound as a colorless solid having the following structural formula.

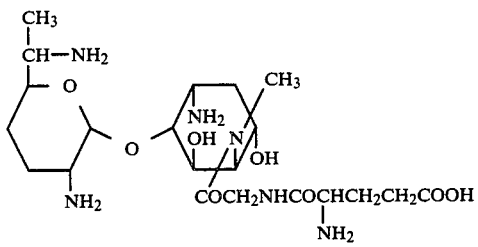

Specific rotation: $[\alpha]_D^{24}+68°$ (c0.5, H$_2$O).

$^1$H-NMR value: $\delta_{D_2O}^{TMS}$ ppm 1.36 (3H, d, J=7 Hz, C—CH$_3$), 2.66 (2H, t, J=7.3 Hz, C—CH$_2$—COOH), 3.18 (3H, s, N—CH$_3$), 5.50 (1H, d, J=3 Hz, H-1').

Elemental analysis for C$_{21}$H$_{40}$N$_6$O$_8$·4HCl·2H$_2$O:

|  | C | H | N | Cl |
|---|---|---|---|---|
| Calculated (%) | 36.74 | 7.05 | 12.24 | 20.66 |
| Found (%) | 36.28 | 6.62 | 12.11 | 20.82 |

EXAMPLE 6

Production of 2''-N-glycyl-5-de-O-methyl-KA-6606I (A) In the same way as in Example 1, (A), 70 mg of 1,2',6'-tris-N-benzyloxycarbonyl-5-de-O-methyl-KA-6606I obtained in Referential Example 1 and 40 mg of the N-hydroxysuccinimide ester of N-benzyloxycarbonylglycine were reacted, and the reaction product was purified by preparative thin-layer chromatography [carrier: silica gel; solvent: chloroform/methanol (8:1)] to give 55 mg of 1,2',6'-tris-N-benzyloxycarbonyl-2''-N-(N-benzyloxycarbonylglycyl)-5-de-O-methyl-KA-6606I as a colorless solid.

Specific rotation: $[\alpha]_D^{20}+41°$ (c1, CHCl$_3$).

$^1$H-NMR value: $\delta_{CDCl_3}^{TMS}$ ppm 1.02 (3H, d, J=7 Hz, C—CH$_3$), 2.92 (3H, s, N—CH$_3$).

Elemental analysis for C$_{50}$H$_{60}$N$_6$O$_{4}$:

|  | C | H | N |
|---|---|---|---|
| Calculated (%) | 61.97 | 6.24 | 8.67 |
| Found (%) | 61.59 | 6.38 | 8.41 |

(B) The N-protected compound obtained in (A) above (41 mg) was reacted and worked up in the same way as in Example 3, (B) to give 25 mg of the hydrochloride of the desired compound as a colorless solid having the following structural formula.

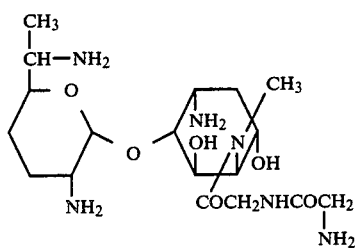

Specific rotation: $[\alpha]_D^{22}+74°$ (c1, H$_2$O).

$^1$H-NMR value: $\delta_{D_2O}^{TMS}$ ppm 1.35 (3H, d, J=7 Hz, C—CH$_3$), 3.19 (3H, s, N—CH$_3$), 3.95 (2H, s, COCH$_2$NH$_2$), 5.50 (1H, d, J=3.5 Hz, H-1').

Elemental analysis for C$_{18}$H$_{36}$N$_6$O$_6$·4HCl·2H$_2$O:

|  | C | H | N | Cl |
|---|---|---|---|---|
| Calculated (%) | 35.19 | 7.22 | 13.68 | 23.08 |
| Found (%) | 34.83 | 7.04 | 13.37 | 23.62 |

EXAMPLE 7

Production of 2''-N-L-alanyl-5-de-O-methyl-KA-6606I (A) In the same way as in Example 1, (A), 35 mg of 1,2',6'-tris-N-benzyloxycarbonyl-5-de-O-methyl-KA-6606I obtained in Referential Example 1 and 34 mg of the N-hydroxysuccinimide ester of N-benzyloxycarbonyl-L-alanine were reacted, and the reaction product was purified by preparative thin-layer chromatography [carrier: silica gel; solvent: chloroform/methanol (9:1)] to give 25 mg of 1,2',6'-tris-N-benzyloxycarbonyl-2''-N-(N-benzyloxycarbonyl-L-alanyl)-5-de-O-methyl-KA-6606I as a colorless solid.

Specific rotation: $[\alpha]_D^{22}+35°$ (c1, CHCl$_3$).

$^1$H-NMR value: $\delta_{CDCl_3}^{TMS}$ ppm 1.03 (3H, d, J=6 Hz, C$^{6'}$—CH$_3$), 1.28 (3H, d, J=6 Hz, Ala—CH$_3$), 2.91, 3.06 (total 3H, s, N—CH$_3$, rotational isomer).

Elemental analysis for C$_{51}$H$_{62}$N$_6$O$_{14}$:

|  | C | H | N |
|---|---|---|---|
| Calculated (%) | 62.31 | 6.36 | 8.55 |
| Found (%) | 62.08 | 6.29 | 8.18 |

(B) The N-protected compound obtained in (A) above (25 mg) was reacted and worked up in the same way as in Example 3, (B) to give 14 mg of the hydrochloride of the desired compound as a colorless solid having the following structural formula.

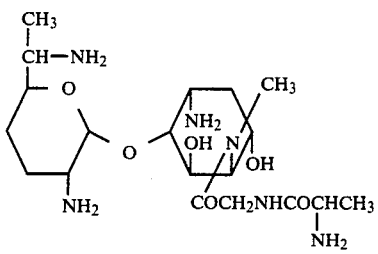

Specific rotation: $[\alpha]_D^{20} +65°$ (c0.6, $H_2O$).

$^1$H-NMR value: $\delta_{D_2O}^{TMS}$ ppm 1.35 (3H, d, J=7 Hz, $C^{6'}$—$CH_3$), 1.60 (3H, d, J=7 Hz, Ala—$CH_3$), 3.18 (3H, s, N—$CH_3$), 5.50 (1H, d, J=3.5 Hz, H-1').

Elemental analysis for $C_{19}H_{38}N_6O_6.4HCl.H_2O$:

|  | C | H | N | Cl |
|---|---|---|---|---|
| Calculated (%) | 37.38 | 7.27 | 13.77 | 23.23 |
| Found (%) | 36.96 | 7.21 | 13.51 | 24.03 |

EXAMPLE 8

Production of 2''-N-beta-alanyl-5-de-O-methyl-KA-6606I (A) In the same way as in Example 1, (A), 35 mg of 1,2',6'-tris-N-benzyloxycarbonyl-5-de-O-methyl-KA-6606I obtained in Referential Example 1 and 34 mg of the N-hydroxysuccinimide ester of N-benzyloxycarbonyl-betaalanine were reacted, and the reaction mixture was purified by preparative thin-layer chromatography [carrier: silica gel; solvent: chloroform/methanol (9:1)] to give 30 mg of 1,2',6'-tris-N-benzyloxycarbonyl-2''-N-(N-benzyloxycarbonyl beta-alanyl)-5-de-O-methyl-KA-6606I as a colorless solid.

Specific rotation: $[\alpha]_D^{21} +36°$ (c1, $CHCl_3$).

$^1$H-NMR value: $\delta_{CDCl_3}^{TMS}$ ppm 1.03 (3H, d, J=6.5 Hz, C—$CH_3$), 2.96, 3.06 (total 3H, s, N—$CH_3$, rotational isomer).

Elemental analysis for $C_{51}H_{62}N_6O_{14}$:

|  | C | H | N |
|---|---|---|---|
| Calculated (%) | 62.31 | 6.36 | 8.55 |
| Found (%) | 62.53 | 6.30 | 8.06 |

(B) The N-protected compound obtained in (A) above (30 mg) was reacted and worked up in the same way as in Example 3, (B) to give 15 mg of the hydrochloride of the desired compound as a colorless solid having the following structural formula.

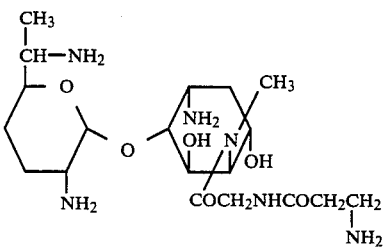

Specific rotation: $[\alpha]_D^{20} +62°$ (c0.65, $H_2O$).

$^1$H-NMR value: $\delta_{D_2O}^{TMS}$ ppm 1.34 (3H, d, J=7 Hz, C—$CH_3$), 2.80 (2H, t, J=6.7 Hz, $COCH_2CH_2NH_2$), 3.30 (2H, t, J=6.7 Hz, $COCH_2CH_2NH_2$), 3.15 (3H, s, N—$CH_3$), 5.48 (1H, d, J=3.5 Hz, H-1').

Elemental analysis for $C_{19}H_{38}N_6O_6.4HCl.H_2O$:

|  | C | H | N | Cl |
|---|---|---|---|---|
| Calculated (%) | 37.38 | 7.27 | 13.17 | 23.23 |
| Found (%) | 36.82 | 7.26 | 13.51 | 23.85 |

EXAMPLE 9

Production of 2''-N-(L-aspartyl-L-lysyl)-5-de-O-methyl-KA-6606I (A) In the same way as in Example 1, (A), 140 mg of 1,2',6'-tris-N-benzyloxycarbonyl-5-de-O-methyl-KA-6606I obtained in Referential Example 1 and 200 mg of the N-hydroxysuccinimide ester of $N^\epsilon$-benzyloxycarbonyl-$N^{\alpha}$-p-methoxybenzyloxycarbonyl-L-lysine were reacted, and the reaction product was purified by silica gel column chromatography [solvent: chloroform/methanol (40:1)] to give 141 mg of 1,2',6'-tris-N-benzyloxycarbonyl-2''-N-$N^\epsilon$-benzyloxycarbonyl-$N^\alpha$-p-methoxybenzyloxycarbonyl-L-lysyl)-5-de-O-methyl-KA-6606I as a colorless solid.

Specific rotation: $\epsilon_D^{25} +23°$ (c2, $CHCl_3$).

$^1$H-NMR value: $\delta_{CDCl_3}^{TMS}$ ppm 1.04 (3H, d, J=6 Hz, C—$CH_3$), 2.90, 3.04 (total 3H, s, N—$CH_3$, rotational isomer), 6.79, 7.21 (each 2H, d, J=9 Hz, p-methoxybenzyl aromatic ring H).

Elemental analysis for $C_{63}H_{77}N_7O_{17}$:

|  | C | H | N |
|---|---|---|---|
| Calculated (%) | 62.83 | 6.44 | 8.14 |
| Found (%) | 62.48 | 6.52 | 7.97 |

(B) The 2''-N-lysyl compound obtained in (A) above (70 mg) was dissolved in 1.4 ml of acetic acid, and 133 mg of p-toluenesulfonic acid monohydrate and 40 mg of anisole were added. The mixture was left to stand at room temperature for 4 hours. The reaction mixture was concentrated to dryness. The residue was dissolved in chloroform, washed with a 2N aqueous solution of sodium hydroxide and water, and dried. The solvent was evaporated to give a crude product resulting from the elimination of p-methoxybenzyloxycarbonyl.

The product was dissolved in 3 ml of dioxane, and 37 mg of the N-hydroxysuccinimide ester of N-benzyloxycarbonyl-beta-O-benzyl-L-aspartic acid and 0.05 ml of triethylamine were added. The mixture was stirred overnight at room temperature.

The reaction mixture was concentrated to dryness, and the residue was dissolved in chloroform. The chloroform solution was washed with water, dried and purified by preparative thin-layer chromatography [carrier: silica gel; solvent: chloroform/methanol (10:1)] to give 27 mg of 1,2',6'-tris-N-benzyloxycarbonyl-2''-N-[$N^\alpha$-(N-benzyloxycarbonyl-beta-O-benzyl-L-aspartyl)-$N^\epsilon$-benzyloxycarbonyl-L-lysyl]-5-de-O-methyl-KA-6606I as a colorless solid.

Specific rotation: $[\alpha]_D^{22} +26°$ (c1, $CHCl_3$).

$^1$H-NMR value: $\delta_{CDCl_3}^{TMS}$ ppm 1.05 (3H, d, J=6 Hz, C—$CH_3$), 2.92, 3.04 (total 3H, s, N—$CH_3$, rotational isomer).

Elemental analysis for $C_{73}H_{86}N_8O_{19}$:

| | C | H | N |
|---|---|---|---|
| Calculated (%) | 63.56 | 6.28 | 8.12 |
| Found (%) | 63.31 | 5.95 | 7.91 |

(C) The N,O-protected compound obtained in (B) above (27 mg) was reacted and worked up in the same way as in Example 3, (B) to give 13 mg of the hydrochloride of the desired compound as a colorless solid having the following structural formula.

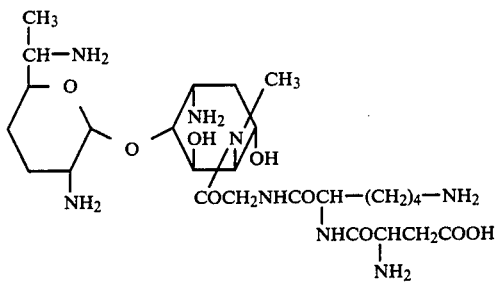

Specific rotation $[\alpha]_D^{24} + 48°$ (c0.5, H$_2$O).

$^1$H-NMR value: $\delta_{D_2O}^{TMS}$ ppm 1.35 (3H, d, J=7 Hz, C—CH$_3$), 3.16 (3H, s, N—CH$_3$), 5.48 (1H, d, J=3.5 Hz, H-1').

Elemental analysis for C$_{26}$H$_{50}$N$_8$O$_9$.5HCl.2H$_2$O:

| | C | H | N | Cl |
|---|---|---|---|---|
| Calculated (%) | 37.31 | 7.10 | 13.39 | 21.18 |
| Found (%) | 36.88 | 7.18 | 13.21 | 21.66 |

EXAMPLE 10

Production of 2''-N-(L-aspartyl-L-tyrosyl)-5-de-O-methyl-KA-6606I (A) In the same way as in Example 1, (A), 140 mg of 1,2',6'-tris-N-benzyloxycarbonyl-5-de-O-methyl-KA-6606I obtained in Referential Example 1 and 250 mg of the N-hydroxysuccinimide ester of N-p-methoxybenzyloxycarbonyl-L-tyrosine, and the reaction product was purified by silica gel column chromatography [solvent: chloroform/methanol (30:1)] to give 110 mg of 1,2',6'-tris-N-benzyloxycarbonyl-2''-N-(N-p-methoxybenzyloxycarbonyl-L-tyrosyl)-5-de-O-methyl-KA-6606I as a colorless solid.

Specific rotation: $[\alpha]_D^{23} + 26°$ (c1, CHCl$_3$).

$^1$H-NMR value: $\delta_D^{TMS}$ ppm 1.02 (3H, d, J=6 Hz, C—CH$_3$), 2.82, 2.98 (total 3H, s, N—CH$_3$, rotational isomer), 6.64, 6.87 (each 2H, d, J=8 Hz, tyrosyl aromatic ring H), 6.79, 7.12 (each 2H, d, J=9 Hz, p-methoxybenzyl aromatic ring H).

Elemental analysis for C$_{58}$H$_{68}$N$_6$O$_{16}$:

| | C | H | N |
|---|---|---|---|
| Calculated (%) | 63.03 | 6.20 | 7.60 |
| Found (%) | 63.15 | 6.13 | 7.28 |

(B) The 2''-N-tyrosyl compound obtained in (A) above (100 mg) was reacted and worked up in the same way as in Example 9, (B) to give 65 mg of 1,2',6'-tris-N-benzyloxy-carbonyl-2''-N-[N-(N-benzyloxycarbonyl-beta-O-benzyl-L-aspartyl)-L-tyrosyl]-5-de-O-methyl-KA-6606I as a colorless solid.

Specific rotation: $[\alpha]_D^{25} + 16°$ (c1, CHCl$_3$).

$^1$H-NMR value $\delta_{CDCl_3}^{TMS}$ ppm 1.06 (3H, d, J=6 Hz, C—CH$_3$), 2.88, 3.01 (total 3H, s, N—CH$_3$, rotational isomer), 6.84, 7.12 (each 2H, d, J=8 Hz, tyrosyl aromatic ring H).

Elemental analysis for C$_{68}$H$_{77}$N$_7$O$_{18}$:

| | C | H | N |
|---|---|---|---|
| Calculated (%) | 63.79 | 6.06 | 7.66 |
| Found (%) | 63.51 | 5.82 | 7.23 |

(C) The N-protected compound obtained in (B) (24 mg) was reacted and worked up in the same way as in Example 3, (B) to give 10 mg of the hydrochloride of the desired compound as a colorless solid having the following structural formula.

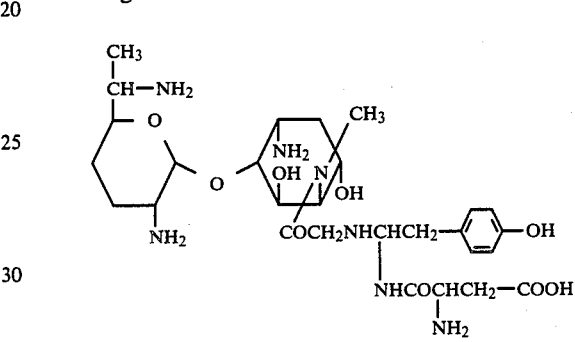

Specific rotation: $[\alpha]_D^{24} + 56°$ (c0.5, H$_2$O).

$^1$H-NMR value: $\delta_{D_2O}^{TMS}$ ppm 1.35 (3H, d, J=7 Hz, C—CH$_3$), 3.15 (3H, s, N—CH$_3$), 5.48 (1H, d, J=3.5 Hz, H-1'), 7.15, 7.39 (each 2H, d, J=8.5 Hz, tyrosyl aromatic ring H).

Elemental analysis for C$_{29}$H$_{47}$N$_7$O$_{10}$.4HCl.H$_2$O:

| | C | H | N | Cl |
|---|---|---|---|---|
| Calculated (%) | 42.60 | 6.53 | 11.99 | 17.35 |
| Found (%) | 41.98 | 6.41 | 12.13 | 17.86 |

EXAMPLE 11

Production of 2''-N-(beta-O-methyl-L-aspartyl-L-tyrosyl)-5-O-methyl-KA-6606I (A) In the same way as in Example 9, (B), 65 mg of 1,2',6'-tris-N-benzyloxycarbonyl-2''-N-(N-p-methoxybenzyloxycarbonyl-L-tyrosyl)-5-O-methyl-KA-6606I obtained in Example 10, (A) and 40 mg of the N-hydroxysuccinimide ester of N-benzyloxycarbonyl-beta-O-methyl-L-aspartic acid were reacted, and the reaction mixture was purified by preparative thin-layer chromatography [carrier: silica gel; solvent: chloroform/methanol (10:1)] to give 20 mg of 1,2',6'-tris-N-benzyloxycarbonyl-2''-N-[N-(N-benzyloxycarbonyl-beta-O-methyl-L-aspartyl)-L-tyrosyl]-5-de-O-methyl-KA-6606I as a colorless solid.

Specific rotation: $[\alpha]_D^{25} + 21°$ (c1, CHCl$_3$).

$^1$H-NMR value $\delta_{CDCl_3}^{TMS}$ ppm 1.06 (3H, d, J=6 Hz, C—CH$_3$), 2.90, 3.02 (total 3H, s, N—CH$_3$, rotational isomer), 3.61 (3H, s, —COO—CH$_3$), 6.92, 7.14 (each 2H, d, J=8 Hz, tyrosyl aromatic ring H).

Elemental analysis for $C_{62}H_{73}N_7O_{18}$:

|  | C | H | N |
|---|---|---|---|
| Calculated (%) | 61.83 | 6.11 | 8.14 |
| Found (%) | 62.08 | 6.23 | 7.85 |

(B) The N-protected compound obtained in (A) (20 mg) was reacted and worked up in the same way as in Example 3, (B) to give 12 mg of the hydrochloride of the desired compound as a colorless solid having the following structural formula.

[Structural formula shown]

Specific rotation: $[\alpha]_D^{25} + 60°$ (c0.5, $H_2O$)

$^1$H-NMR value: $\delta_{D_2O}^{TMS}$ ppm 1.35 (3H, d, J=6.5 Hz, C—$CH_3$), 3.15 (3H, s, N—$CH_3$), 3.74 (3H, s, $COOCH_3$), 5.49 (1H, d, J=3 Hz, H-1'), 7.15, 7.39 (each 2H, d, J=8.5 Hz, tyrosyl aromatic ring H).

Elemental analysis for $C_{30}H_{49}N_7O_{10}\cdot 4HCl\cdot H_2O$:

|  | C | H | N | Cl |
|---|---|---|---|---|
| Calculated (%) | 43.33 | 6.67 | 11.79 | 17.05 |
| Found (%) | 43.58 | 6.41 | 11.38 | 17.29 |

EXAMPLE 12

Production of 2''-N-(beta-O-methyl-L-aspartyl-L-lysyl)-5-de-O-methyl-KA-6606I (A) In the same way as in Example 9, (B), 66 mg of 1,2',6'-tris-N-benzyloxycarbonyl-2''-N-(N$^\epsilon$-benzyloxycarbonyl-N$^\alpha$-p-methoxybenzyloxycarbonyl-L-lysyl)-5-O-methyl-KA-6606I obtained in Example 9, (A) and 40 mg of the N-hydroxysuccinimide ester of N-benzyloxycarbonyl-beta-O-methyl-L-aspartic acid were reacted, and the reaction mixture was purified by preparative thin-layer chromatography [carrier: silica gel; solvent: chloroform/methanol (10:1)] to give 26 mg of 1,2',6'-tris-N-benzyloxycarbonyl-'''-N-[N$^\epsilon$-(N-benzyloxycarbonyl-beta-O-methyl-L-aspartyl)-benzyloxycarbonyl-L-lysyl]-5-de-O-methyl-KA-6606I as a colorless solid.

Specific rotation: $[\alpha]_D^{25} + 20°$ (c0.5, $H_2O$).

$^1$H-NMR value: $\delta_{CDCl_3}^{TMS}$ ppm 1.05 (3H, d, J=6 Hz, C—$CH_3$), 2.90, 3.02 (total 3H, s, N—$CH_3$, rotational isomer). 3.60 (3H, s, $COOCH_3$).

Elemental analysis for $C_{67}H_{82}N_8O_{19}$:

|  | C | H | N |
|---|---|---|---|
| Calculated (%) | 61.74 | 6.34 | 8.60 |
| Found (%) | 61.60 | 6.22 | 8.38 |

(B) The N-protected compound obtained in (A) above (26 mg) was reacted and worked up in the same way as in Example 3, (B) to give 15 mg of the hydrochloride of the desired compound having the following structural formula.

[Structural formula shown]

Specific rotation: $[\alpha]_D^{25} + 54°$ (c0.5, $H_2O$).

$^1$H-NMR value: $\delta_{D_2O}^{TMS}$ ppm 1.35 (3H, d, J=7 Hz, C—$CH_3$), 3.17 (3H, s, N—$CH_3$), 3.76 (3H, s, $COOCH_3$), 5.49 (1H, d, J=3.5 Hz, H-1').

Elemental analysis for $C_{27}H_{52}N_8O_9\cdot 5HCl\cdot 2H_2O$:

|  | C | H | N | Cl |
|---|---|---|---|---|
| Calculated (%) | 38.10 | 7.22 | 13.17 | 20.83 |
| Found (%) | 37.78 | 6.91 | 13.10 | 21.25 |

EXAMPLE 13

Production of 2''-N-L-aspartyl-5-demethoxy-KA-6606I (A) In the same way as in Example 1, (A), 50 mg of 1,2',6'-tris-N-benzyloxycarbonyl-5-demethoxy-KA-6606I obtained in Referential Example 2 and 50 mg of the N-hydroxysuccinimide ester of N-benzyloxycarbonyl-beta-O-benzyl-L-asparatic acid were reacted, and the reaction product was purified by preparative thin-layer chromatography [carrier: silica gel; solvent: chloroform/methanol (20:1)] to give 35 mg of 1,2',6'-tris-N-benzyloxycarbonyl-2''-N-(N-benzyloxycarbonyl-beta-O-benzyl-L-aspartyl)-5-demethoxy-KA-6606I as a colorless solid.

Specific rotation: $[\alpha]_D^{21} + 35°$ (c1, $H_2O$).

$^1$H-NMR value: $\delta_{CDCl_3}^{TMS}$ ppm 1.06 (3H, d, J=7 Hz, C—$CH_3$), 2.80 (3H, s, N—$CH_3$).

Elemental analysis for $C_{59}H_{68}N_6O_{15}$:

|  | C | H | N |
|---|---|---|---|
| Calculated (%) | 64.35 | 6.22 | 7.63 |
| Found (%) | 64.17 | 6.22 | 7.51 |

(B) The N,O-protected compound obtained in (A) above (34 mg) was reacted and worked up in the same way as in Example 3, (B) to give 19 mg of the hydrochloride of the desired compound as a colorless solid having the following structural formula.

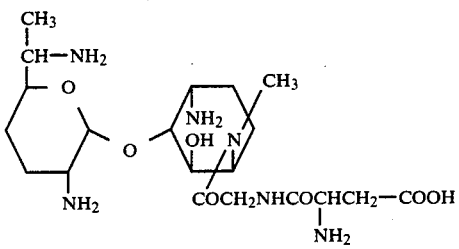

Specific rotation: $[\alpha]_D^{21} +85°$ (c1, H$_2$O).

$^1$H-NMR value: $\delta_{D_2O}^{TMS}$ ppm 1.34 (3H, d, J=7 Hz, C—CH$_3$), 3.08 (3H, s, N—CH$_3$), 3.12 (2H, m, —CH$_2$—COOH).

Elemental analysis for C$_{20}$H$_{38}$N$_6$O$_7$.4HCl.2H$_2$O:

|  | C | H | N | Cl |
|---|---|---|---|---|
| Calculated (%) | 36.59 | 7.06 | 12.80 | 21.60 |
| Found (%) | 36.23 | 7.18 | 12.49 | 22.02 |

EXAMPLE 14

Production of 2″-N-L-glutamyl-KA-7038I (A) Two hundred milligrams of KA-7038II was dissolved in 6 ml of methanol, and 312 mg of nickel (II) acetate tetrahydrate was added. The mixture was stirred at room temperature for 30 minutes, and then under ice cooling, 510 mg of N-benzyloxycarbonyloxysuccinimide was added, and the mixture was stirred for 3 hours.

Concentrated aqueous ammonia (1.5 ml) was added to the reaction mixture, and the mixture was stirred at room temperature for 30 minutes and then concentrated to dryness. The residue was dissolved in chloroform, washed with 3N aqueous ammonia, and dried. The solvent was evaporated to give crude 1,2′,6′-tris-N-benzyloxycarbonyl-KA-7038II.

The crude product was dissolved in 10 ml of dioxane, and 420 mg of the N-hydroxysuccinimide ester of N-diphenylphosphinothioylglycine and 0.1 ml of triethylamine were added. The mixture was left to stand overnight at 37° C.

The reaction mixture was concentrated to dryness. The residue was dissolved in chloroform, washed with water and dried. The solvent was evaporated. The residue was purified by silica gel column chromatography (chloroform/acetone 20:1→10:1) to give 370 mg of 1,2′,6′-tris-N-benzyloxycarbonyl-2″-N-diphenylphosphinothioyl-KA-7038I as a colorless solid.

Specific rotation: $[\alpha]_D^{23} +52°$ (c1, CHCl$_3$).

$^1$H-NMR value: $\delta_{CDCl_3}^{TMS}$ ppm 2.94 (6H, s, N—CH$_3$), 3.24 (3H, s, O—CH$_3$).

Elemental analysis for C$_{53}$H$_{62}$N$_5$O$_{11}$PS:

|  | C | H | N |
|---|---|---|---|
| Calculated (%) | 63.14 | 6.20 | 6.95 |
| Found (%) | 62.86 | 5.93 | 6.81 |

(B) The 2″-N-protected compound obtained in (A) above (300 mg) was dissolved in 7 ml of tetrahydrofuran, and 1.5 ml of concentrated hydrochloric acid was added. The solution was left to stand at room temperature for 6 hours. The reaction mixture was neutralized with concentrated aqueous ammonia, and the solvent was evaporated. The residue was dissolved in chloroform, washed with a 1N aqueous solution of sodium hydroxide and then with water, and dried. The solvent was evaporated to give crude 1,2′,6′-tris-N-benzyloxycarbonyl-KA-7038I.

The crude product was dissolved in 8 ml of dioxane, and 185 mg of the N-hydroxysuccinimide ester of N-benzyloxycarbonyl-gamma-O-benzyl-L-glutamic acid and 0.2 ml of triethylamine were added. The mixture was left to stand overnight at room temperature. The reaction mixture was concentrated to dryness. The residue was dissolved in chloroform, washed with water, and dried. The solvent was then evaporated. The residue was purified by silica gel column chromatography [solvent: chloroform/methanol (100:1)] to give 140 mg of 1,2′,6′-tris-N-benzyloxycarbonyl-2″-N-(N-benzyloxycarbonyl-gamma-O-benzyl-L-glutamyl)-KA-7038I as a colorless solid.

Specific rotation: $[\alpha]_D^{22} +49°$ (c1, CHCl$_3$).

$^1$H-NMR value: $\delta_{CDCl_3}^{TMS}$ ppm 2.92 (6H, s, N—CH$_3$), 3.22 (3H, s, O—CH$_3$).

Elemental analysis for C$_{61}$H$_{72}$N$_6$O$_{16}$:

|  | C | H | N |
|---|---|---|---|
| Calculated (%) | 63.97 | 6.34 | 7.34 |
| Found (%) | 64.18 | 6.25 | 6.89 |

(C) The N,O-protected compound obtained in (B) above (70 mg) was reacted and worked up in the same way as in Example 3, (B) to give 36 mg of the hydrochloride of 2″-N-L-glutamyl-KA-7038I as a colorless solid having the following structural formula.

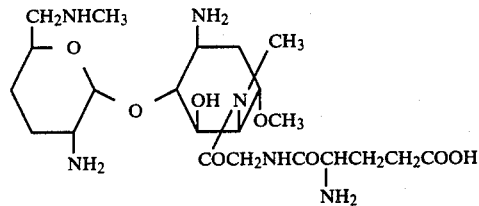

Specific rotation: $[\alpha]_D^{21} +82°$ (c1, H$_2$O).

$^1$H-NMR value: $\delta_{D_2O}^{TMS}$ ppm 2.76 (3H, s, 6′—N—CH$_3$), 3.13 (3H, s, 4—N—CH$_3$), 5.30 (1H, d, J=3.3 Hz, H—1′), 2.68 (2H, t, J=7.3 Hz, —CH$_2$—COOH).

Elemental analysis for C$_{22}$H$_{42}$N$_6$O$_8$.4HCl.2H$_2$O.

|  | C | H | N | Cl |
|---|---|---|---|---|
| Calculated (%) | 37.72 | 7.19 | 12.00 | 20.25 |
| Found (%) | 37.68 | 7.28 | 11.62 | 20.48 |

EXAMPLE 15

Production of 2″-N-glycyl-5-de-O-methyl-KA-6606I

Seventy milligrams of 1,2′,6′-tris-N-benzyloxycarbonyl-5-de-O-methyl-KA-6606II was dissolved in 2 ml of dioxane, and 50 mg of the N-hydroxysuccinimide ester of N-benzyloxycarbonylglycylglycine and 0.03 ml of triethylamine were added. The mixture was left to stand overnight at 37° C. The reaction mixture was concentrated to dryness. The residue was dissolved in chloroform, washed with water and dried. The solution was purified by preparative thin-layer chromatography [carrier: silica gel; solvent: chloroform/methanol (8:1)]

to give 51 mg of 1,2',6'-tris-N-benzyloxycarbonyl-2''-N-(N-benzyloxycarbonylglycyl)-5-de-O-methyl-KA-6606I as a colorless solid. This compound agreed with the compound obtained in Example 6, (A) in thin-layer chromatography, $^1$H-NMR values, IR values and specific rotation.

The compound was then subjected to the same procedure as in Example 6, (B) to give the final desired compound.

EXAMPLE 16

Production of 4-N-(glycyl-beta-alanyl)-5-de-O-methyl-KA-6606II (A) Seventy milligrams of 1,2',6'-tris-N-benzyloxycarbonyl-5-de-O-methyl-KA-6606II was dissolved in 2.1 ml of dioxane, and 42 mg of the N-hydroxysuccinimide ester of N-benzyloxycarbonylglycyl-beta-alanine and 0.03 ml of triethylamine were added. The mixture was left to stand overnight at 37° C.

The reaction mixture was concentrated to dryness, and the residue was dissolved in chloroform, washed with water and dried. The solution was purified by preparative thin-layer chromatography [carrier: silica gel; solvent: chloroform/methanol (8:1)] to give 48 mg of 1,2',6'-tris-N-benzyloxycarbonyl-4-N-(N-benzyloxycarbonylglycyl-betaalanyl)-5-de-O-methyl-KA-6606II as a colorless solid.

Specific rotation: $[\alpha]_D^{21} + 38°$ (c1, CHCl$_3$).

$^1$H-NMR value: $\delta_{CDCl_3}^{TMS}$ ppm 1.03 (3H, d, J=6.5 Hz, C—CH$_3$), 2.95, 3.05 (total 3H, s, N—CH$_3$, rotational isomer).

Elemental analysis for C$_{51}$H$_{62}$N$_6$O$_{14}$:

|  | C | H | N |
|---|---|---|---|
| Calculated (%) | 62.31 | 6.36 | 8.55 |
| Found (%) | 61.92 | 6.21 | 8.18 |

(B) The N-protected compound obtained in (A) above (45 mg) was reacted and worked up in the same way as in Example 3, (B) to give 22 mg of the hydrochloride of 4-N-(glycyl-beta-alanyl)-5-de-O-methyl-KA-6606II as a colorless solid having the following structural formula.

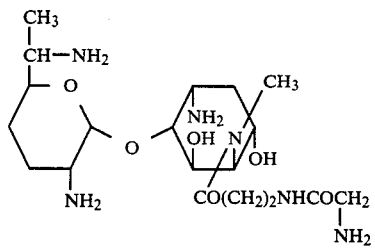

Specific rotation: $[\alpha]_D° + 60°$ (c1, H$_2$O).

$^1$H-NMR value: $\delta_{D_2}^{OTMS}$ ppm 1.35 (3H, d, J=7 Hz, C—CH$_3$), 3 18 (3H, s, N—CH$_3$), 3.93 (2H, s, COCH$_2$NH$_2$), 5.49 (1H, d, J=3.5 Hz, H-1').

Elemental analysis for C$_{19}$H$_{38}$N$_6$O$_6$.4HCl.H$_2$O:

|  | C | H | N | Cl |
|---|---|---|---|---|
| Calculated (%) | 37.38 | 7.27 | 13.77 | 23.23 |
| Found (%) | 37.21 | 7.04 | 13.19 | 23.85 |

EXAMPLE 17

Production of 2''-N-L-phenylalanyl-5-de-O-methyl-KA-6606I (A) In the same way as in Example 1, (A), 300 mg of 1,2',6'-tris-N-benzyloxycarbonyl-5-de-O-methyl-KA-6606I obtained in Referential Example 1 and 145 mg of the hydroxysuccinimide ester of N-benzyloxycarbonylphenylalanine were reacted, and the reaction mixture was purified by silica gel column chromatography [solvent: chloroform/methanol (98:2)] to give 255 mg of 1,2',6'-tris-N-benzyloxycarbonyl-2''-N-(N-benzyloxycarbonyl-L-phenylalanyl)-5-de-O-methyl-KA-6606I as a colorless solid.

Specific rotation: $[\alpha]_D^{17} + 31°$ (c3, CHCl$_3$).

$^1$H-NMR value: $\delta_{CDCl_3}^{TMS}$ ppm 1.05 (3H, br.d, C—CH$_3$), 2.91, 3.07 (total 3H, s, N—CH$_3$, rotational isomer).

Elemental analysis for C$_{57}$H$_{66}$N$_6$O$_{14}$:

|  | C | H | N |
|---|---|---|---|
| Calculated (%) | 64.64 | 6.28 | 7.93 |
| Found (%) | 64.35 | 6.09 | 7.79 |

(B) The N-protected compound obtained in (A) above (255 mg) was worked up in the same way as in Example 3, (B) to give 160 mg of the hydrochloride of the desired compound as a colorless solid having the following structural formula

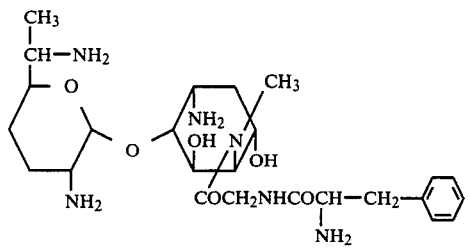

Specific rotation: $[\alpha]_D^{20} + 101°$ (c0.98, H$_2$O).

$^1$H-NMR value: $\delta_{D_2}^{OTMS}$ ppm 1.35 (3H, d, J=7 Hz, C—CH$_3$), 3.16 (3H, s, N—CH$_3$), 5.49 (1H, d, J=3.5 Hz, H-1'), 7.38 (5H, m, aromatic H).

Elemental analysis for C$_{25}$H$_{42}$N$_6$O$_6$.4HCl.H$_2$O:

|  | C | H | N | Cl |
|---|---|---|---|---|
| Calculated (%) | 43.74 | 7.05 | 12.24 | 20.66 |
| Found (%) | 43.37 | 7.25 | 12.01 | 21.02 |

EXAMPLE 18

Production of 2''-N-L-seryl-5-de-O-methyl-KA-606I (A) In the same way as in Example 1, (A), 337 mg of 1,2',6'-tris-N-benzyloxycarbonyl-5-de-O-methyl-KA-6606I obtained in Referential Example 1 and 131 mg of the N-hydroxysuccinimide ester of N-benzyloxycarbonylserine were reacted, and the reaction mixture was purified by silica gel column chromatography [solvent: chloroform/methanol (97:3)] to give 267 mg of 1,2',6'-tris-N-benzyloxycarbonyl-2''-N-benzyloxycarbonyl-L-seryl)-5-de-O-methyl-KA-6606I as a colorless solid.

Specific rotation: $[\alpha]_D^{21} + 39°$ (c2, CHCl$_3$).

IR value: $\nu_{max}^{CHCl_3}$ cm$^{-1}$ 1628 (amide I).

$^1$H-NMR value: $\delta_{CDCl_3}{}^{TMS}$ ppm 1.03 (3H, br.d, C—CH$_3$), 2.89, 3.01 (total 3H, s, N—CH$_3$, rotational isomer).

Elemental analysis for C$_{51}$H$_{62}$N$_6$O$_{15}$:

|  | C | H | N |
|---|---|---|---|
| Calculated (%) | 61.31 | 6.26 | 8.41 |
| Found (%) | 61.48 | 6.04 | 8.09 |

(B) The N-protected compound obtained in (A) above (225 mg) was reacted and worked up in the same way as in Example 3, (B) to give 135 mg of the hydrochloride of the desired compound as a colorless solid having the following structural formula.

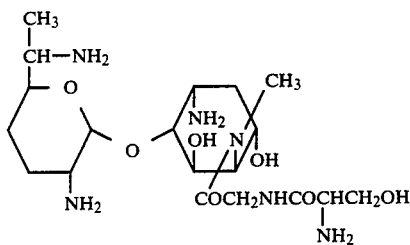

Specific rotation: $[\alpha]_D{}^{20}+84°$ (c1.07, H$_2$O).

$^1$H-NMR value: $\delta_{D_2O}{}^{OTMS}$ ppm 1.35 (3H, d, J=7 Hz, C—CH$_3$), 3.18 (3H, s, N—CH3), 5.49 (1H, d, J=3.5 Hz, H-1').

Elemental analysis for C$_{19}$H$_{38}$N$_6$O$_7$.4HCl.H$_2$O:

|  | C | H | N | Cl |
|---|---|---|---|---|
| Calculated (%) | 36.43 | 7.08 | 13.42 | 22.64 |
| Found (%) | 36.20 | 7.40 | 13.58 | 22.29 |

EXAMPLE 19

Production of
2″-N-L-tryptophyl-5-de-O-methyl-KA-6606I (A) In the same way as in Example 1, (A), 300 mg of 1,2′,6′-tris-N-benzyloxycarbonyl-5-de-O-methyl-KA-6606I obtained in Referential Example 1 and 168 mg of the hydroxysuccinimide ester of N-benzyloxycarbonyl-L-tryptophan were reacted, and the reaction product was purified by silica gel column chromatography [solvent: chloroform/methanol (97:3)] to give 191 mg of 1,2′,6′-tris-N-benzyloxycarbonyl-2″-N-(N-benzyloxycarbonyl-L-tryptophyl)-5-de-O-methyl-KA-6606I as a colorless solid.

Specific rotation: $[\alpha]_D{}^{19}+31°$ (c3, CHC$_3$).

$^1$H-NMR value: $\delta_{CDCl_3}{}^{TMS}$ ppm 1.02 (3H, br.d, C—CH$_3$), 2.78, 2.94 (total 3H, s, N—CH$_3$, rotational isomer).

Elemental analysis for C$_{59}$H$_{67}$N$_7$O$_{14}$:

|  | C | H | N |
|---|---|---|---|
| Calculated (%) | 64.53 | 6.15 | 8.93 |
| Found (%) | 64.28 | 6.33 | 9.14 |

(B) The N-protected compound obtained in (A) (191 mg) was reacted and worked up in the same way as in Example 3, (B) to give 111 mg of the hydrochloride of the desired compound as a colorless solid having the following structural formula.

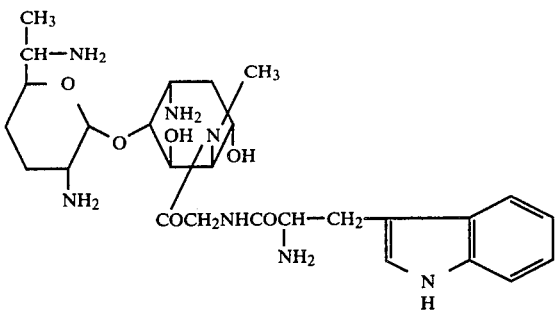

Specific rotation: $[\alpha]_D{}^{20}+100°$ (c1.03, H$_2$O).

$^1$H-NMR value: $\delta_{D_2O}{}^{TMS}$ ppm 1.35 (3H, d, J=7 Hz, C—CH$_3$), 3.11 (3H, s, N—CH$_3$), 5.46 (1H, d, J=3.5 Hz, H-1'), 7.16–7.68 (5H, m, aromatic H).

Elemental analysis for C$_{27}$H$_{43}$N$_7$O$_6$.4HCl.2H$_2$O:

|  | C | H | N | Cl |
|---|---|---|---|---|
| Calculated (%) | 43.61 | 6.91 | 13.19 | 19.07 |
| Found (%) | 43.69 | 7.20 | 13.50 | 18.89 |

EXAMPLE 20

Production of
2″-N-L-methionyl-5-de-O-methyl-KA-6606I (A) In the same way as in Example 1, (A), 394 mg of 1,2′,6′-tris-N-benzyloxycarbonyl-5-de-O-methyl-KA-6606I obtained in Referential Example 1 and 173 mg of the N-hydroxysuccinimide ester of N-benzyloxycarbonyl-L-methionine were reacted, and the reaction product was purified by silica gel column chromatography [solvent: chloroform/methanol (98:2)] to give 309 mg of 1,2′,6′-tris-N-benzyloxycarbonyl-2″-N-(N-benzyloxycarbonyl-L-methionyl)-5-de-O-methyl-KA-6606I as a colorless solid.

Specific rotation: $8\alpha]_D{}^{20}+37°$ (c3, CHCl$_3$).

IR value: $\nu_{max}{}^{CHCl_3}$ cm$^{-1}$ 1635 (amide I).

$^1$H-NMR value: $\delta_{CDCl_3}{}^{TMS}$ ppm 1.03 (3H, d, J=6.5 Hz, C—CH$_3$), 2.02 (3H, s, S—CH$_3$), 2.90, 3.06 (total 3H, s, N—CH$_3$, rotational isomer).

Elemental analysis for C$_{53}$H$_{66}$N$_6$O$_{14}$S:

|  | C | H | N | S |
|---|---|---|---|---|
| Calculated (%) | 61.02 | 6.38 | 8.06 | 3.07 |
| Found (%) | 61.48 | 6.50 | 7.99 | 2.90 |

(B) Methyl ethyl sulfide (1 ml) was added to 309 mg of the N-protected compound obtained in (A) above, and with ice cooling, 3.3 ml of a 25% acetic acid solution of hydrogen bromide was added, and the mixture was stirred for 30 minutes. Ether was added to the reaction mixture, and the resulting precipitate was collected by filtration, washed with ether and dissolved in 40 ml of water. The aqueous solution was neutralized with aqueous ammonia, and adsorbed on a column (1×23 cm) of CM-Sephadex C-25 (NH$_4$+ type). The column was then developed by a concentration gradient method between 0.05N aqueous ammonia and 0.4N aqueous ammonia and fractionated into 4 ml. fractions. Fractions Nos. 31 to 33 were lyophilized, and the resulting powder was dissolved in a small amount of water. The pH of the solution was adjusted to 5.0 with 0.1N hydrochloric acid, and it was again lyophilized to give 41 mg of the hydrochloride of 2''-N-L-methionyl-5-de-O-methyl-KA-6606I as a colorless solid having the following structural formula.

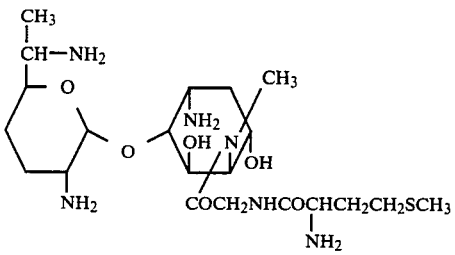

Specific rotation: $[\alpha]_D^{20} + 98°$ (c1.62, H$_2$O).

$^1$H-NMR value: $\delta_{D_2O}^{TMS}$ ppm 1.36 (3H, d, J=7 Hz, C—CH$_3$), 2.16 (3H, s, S—CH$_3$), 3.18 (3H, s, N—CH$_3$), 5.51 (1H, d, J=3.5 Hz, H-1').

Elemental analysis for C$_{21}$H$_{42}$N$_6$O$_6$S.4HCl.H$_2$O.

|  | C | H | N | S | Cl |
|---|---|---|---|---|---|
| Calculated (%) | 37.62 | 7.22 | 12.53 | 4.78 | 21.15 |
| Found (%) | 37.67 | 7.48 | 12.95 | 4.49 | 20.63 |

EXAMPLE 21

Production of 2''-N-L-prolyl-5-de-O-methyl-KA-6606I (A) In the same way as in Example 1, (A), 390 mg of 1,2',6'-tris-N-benzyloxycarbonyl-5-de-O-methyl-KA-6606I and 242 mg of the N-hydroxysuccinimide ester of N-(p-methoxybenzyloxycarbonyl)-L-proline, and the reaction product was purified by silica gel column chromatography [solvent: chloroform/methanol (40:1)] to give 312 mg of 1,2',6'-tris-N-benzyloxycarbonyl-2''-N-[N-(p-methoxybenzyloxycarbonyl)-L-prolyl]-5-de-O-methyl-KA-6606I as a colorless solid.

Specific rotation: $[\alpha]_D^{19} + 14°$ (c1, CHCl$_3$)

IR value: $\nu_{max}^{CHCl_3}$ cm$^{-1}$ 1700, 1635, 1510.

$^1$H-NMR value: $\delta_{CDCl_3}^{TMS}$ ppm 1.04 (3H, d, J=7 Hz, C—CH$_3$), 3.72 (3H, s, O—CH$_3$).

Elemental analysis for C$_{54}$H$_{66}$N$_6$O$_{15}$:

|  | C | H | N |
|---|---|---|---|
| Calculated (%) | 62.41 | 6.40 | 8.09 |
| Found (%) | 61.88 | 6.41 | 7.85 |

(B) The N-protected compound obtained in (A) (269 mg) was reacted and worked up in the same way as in Example 3, (B) to give 138 mg of the hydrochloride of the desired compound as a colorless solid having the following structural formula.

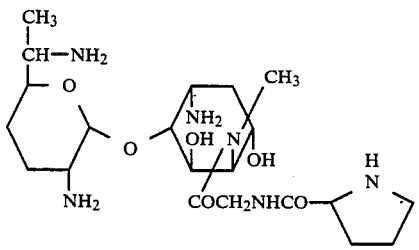

Specific rotation: $[\alpha]_D^{19} + 56°$ (c1, H$_2$O).

IR value: $\nu_{max}^{KBr}$ cm$^{-1}$ 1675, 1620.

$^1$H-NMR value: $\delta_{D_2O}^{TMS}$ ppm 1.34 (3H, d, J=7 Hz, C—CH$_3$), 3.16 (3H, s, N—CH$_3$), 5.50 (1H, d, J=3 Hz, H-1').

Elemental analysis for C$_{21}$H$_{40}$N$_6$O$_6$.4HCl:

|  | C | H | N | Cl |
|---|---|---|---|---|
| Calculated (%) | 40.79 | 7.17 | 13.59 | 22.93 |
| Found (%) | 39.83 | 7.14 | 13.11 | 22.65 |

EXAMPLE 22

Production of 2''-N-(L-glutamyl-L-glulamyl)-5-de-O-methyl-KA-6606I (A) In the same way as in Example 1, (A), 318 mg of 1,2',6'-tris-N-benzyloxycarbonyl-5-de-O-methyl-KA-6606I obtained in Referential Example 1 and 283 mg of the N-hydroxysuccinimide ester of (N-benzyloxycarbonyl-gamma-O-benzyl-L-glutamyl)-gamma-O-benzyl-L-glutamic acid were reacted, and the reaction product was purified by silica gel column chromatography [solvent: chloroform/methanol (98:2)] to give 190 mg of 1,2',6'-tris-N-benzyloxycarbonyl-2''-N-[N-benzyloxycarbonyl-gamma-O-benzyl-L-glutamyl)-(gamma-O-benzyl-L-glutamyl)]-5-de-O-methyl-KA-6606I as a colorless solid.

Specific rotation: $[\alpha]_D^{22} + 20°$ (c2, CHCl$_3$).

IR value: $\nu_{max}^{CHCl_3}$ cm$^{-1}$ 1635 (amide I).

$^1$H-NMR value: $\delta_{CDCl_3}^{TMS}$ ppm 1.04 (3H, br.d, C—CH$_3$), 2.89, 3.01 (total 3H, s, N—CH$_3$, rotational isomer).

Elemental analysis for C$_{72}$H$_{83}$N$_7$O$_{19}$:

|  | C | H | N |
|---|---|---|---|
| Calculated (%) | 64.03 | 6.19 | 7.26 |
| Found (%) | 64.42 | 6.31 | 7.11 |

(B) The N,O-protected compound obtained in (A) above (190 mg) was reacted and worked up in the same way as in Example 3, (B) to give 92 mg of the hydrochloride of the desired compound as a colorless solid having the following structural formula.

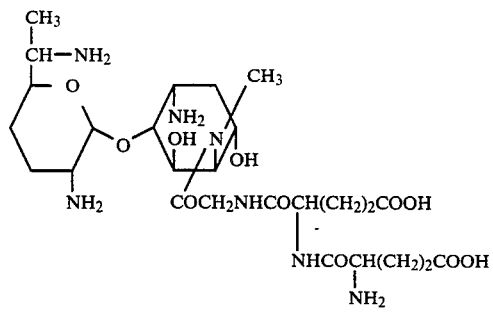

Specific rotation: $[\alpha]_D^{17} + 46°$ (c1, H$_2$O).

$^1$H-NMR value: $\delta_{D_2O}^{TMS}$ ppm 1.36 (3H, d, J=6.8 Hz, C—CH$_3$), 2.55 (4H, t, J=7.4 Hz, —CH$_2$COOH×2), 3.18 (3H, s, N—CH$_3$), 5.50 (1H, d, J=3.5 Hz, H-1').

Elemental analysis for C$_{26}$H$_{47}$N$_7$O$_{11}$.4HCl.2H$_2$O:

|  | C | H | N | Cl |
|---|---|---|---|---|
| Calculated (%) | 38.29 | 6.80 | 12.02 | 17.39 |
| Found (%) | 37.84 | 6.36 | 11.90 | 17.65 |

EXAMPLE 23

Production of 2"-N-(L-leucyl-L-glycyl)-5-de-O-methyl-KA-6606I (A) In the same way as in Example 1, (A), 390 mg of 1,2',6'-tris-N-benzyloxycarbonyl-5-de-O-methyl-KA-6606I obtained in Referential Example 1 and 310 mg of the N-hydroxysuccinimide ester of (N-benzyloxycarbonyl-L-leucyl)glycine were reacted, and the reaction product was purified by silica gel column chromatography [solvent: chloroform/methanol (30:1; 20:1)] to give 308 mg of 1,2',6'-tris-N-benzyloxycarbonyl-2"-N-[(N-benzyloxycarbonyl-L-leucyl)glycyl]-5-de-O-methyl-KA-6606I as a colorless solid.

Specific rotation: $[\alpha]_D^{19} + 34°$ (c1, CHCl$_3$).
IR value: $\nu_{max}^{CHCl_3}$ cm$^{-1}$ 1710, 1510.
$^1$H-NMR value: $\delta_{CDCl_3}^{TMS}$ ppm 1.00 (3H, d, J=6 Hz, C$^{6'}$—CH$_3$), 0.90 [6H, br.d, CH(CH$_3$)$_2$].
Elemental analysis for C$_{56}$H$_{71}$N$_7$O$_{15}$:

|  | C | H | N |
|---|---|---|---|
| Calculated (%) | 62.15 | 6.61 | 9.06 |
| Found (%) | 62.36 | 6.80 | 8.81 |

(B) The N-protected compound obtained in (A) above (300 mg) was reacted and worked up in the same way as in Example 3, (B) to give 193 mg of the hydrochloride of the desired compound as a colorless solid having the following structural formula.

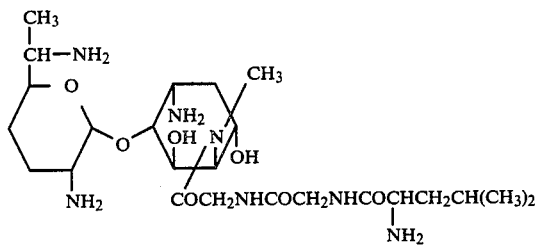

Specific rotation: $[\alpha]_D^{19} + 77°$ (c1, H$_2$O).
IR value: $\nu_{max}^{KBr}$ cm$^{-1}$ 1620 (amide I).
1H-NMR value: $\delta_{D_2O}^{TMS}$ ppm 0.97, 0.99 [each 3H, d, J=8 Hz, CH(CH$_3$)$_2$], 1.35 (3H, d, J=7 Hz, C$^{6'}$—CH$_3$), 3.17 (3H, s, N—CH$_3$), 5.50 (1H, d, J=3.5 Hz, H-1').
Elemental analysis for C$_{24}$H$_{47}$N$_7$O$_7$·4HCl·2H$_2$O:

|  | C | H | N | Cl |
|---|---|---|---|---|
| Calculated (%) | 39.62 | 7.62 | 13.48 | 19.49 |
| Found (%) | 39.86 | 7.50 | 13.62 | 19.21 |

EXAMPLE 24

Production of 2"-N-tryptophyl-5-demethoxy-KA-6606I (A) In 5.9 ml of methanol was dissolved 196 mg of 5-demethoxy-KA-6606II (see Example 1 of Japanese Laid-Open Patent Publication No. 7493/1982), and 484 mg of nickel acetate tetrahydrate was added. The mixture was stirred at room temperature for 1 hour, and 533 mg of N-(benzyloxycarbonyloxy)succinimide was added. The mixture was further stirred at room temperature for 1 hour. To the reaction mixture was added 5.9 ml of a 30% ethanol solution of methylamine, and the mixture was stirred for 30 minutes. The solvent was evaporated. The residue was dissolved in chloroform, washed with 3N aqueous ammonia and water and dried. The solvent was evaporated.

The residue was dissolved in 10 ml of dioxane, and 276 mg of the N-hydroxysuccinimide ester of N-benzyloxycarbonyl-L-tryprophylglycine and 0.2 ml of triethylamine were added. The mixture was left to stand overnight at 37° C. The reaction mixture was concentrated to dryness. The residue was dissovled in chloroform, washed with water, dried and concentrated to dryness. The residue was purified by silica gel column chromatography [solvent: chloroform/methanol (97:3)] to give 342 mg of 1,2',6'-tris-N-benzyloxycarbonyl-2"-N-(N-benzyloxycarbonyl-L-tryptophyl)-5-demethoxy-KA-6606I.

Specific rotation: $[\alpha]_D^{20} + 34°$ (c2, CHCl$_3$).
IR value: $\nu_{max}^{CHCl_3}$ cm$^{-1}$ 1635 (amide I)
$^1$H-NMR value: $\delta_{CDCl_3}^{TMS}$ ppm 1.05 (3H, d, J=6.5 Hz, C—CH$_3$), 2.76, 2.90 (total 3H, s, N—CH$_3$, rotational isomer).
Elemental analysis for C$_{59}$H$_{67}$N$_7$O$_{13}$:

|  | C | H | N |
|---|---|---|---|
| Calculated (%) | 65.48 | 6.24 | 9.06 |
| Found (%) | 65.67 | 6.50 | 8.71 |

(B) The N-protected compound obtained in (A) above (342 mg) was reacted and worked up in the same way as in Example 3, (B) to give 203 mg of the hydrochloride of the desired compound as a colorless solid having the following structural formula.

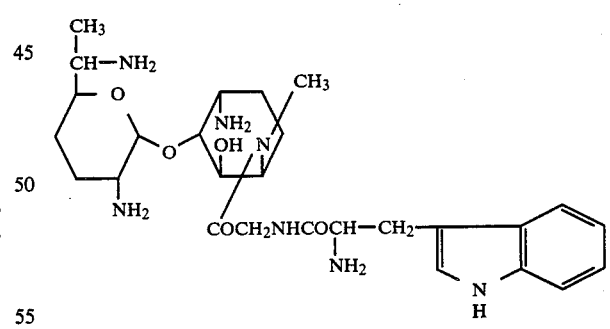

Specific rotation: $[\alpha]_D^{21} + 109°$ (c1.08, H$_2$O).
$^1$H-NMR value: $\delta_{D_2O}^{TMS}$ ppm 1.36 (3H, d, J=6.8 Hz, C—CH$_3$), 2.99 (3H, s, N—CH$_3$), 5.50 (1H, d, J=3.3 Hz, H-1'), 7.19–7.70 (5H, m, aromatic H).
Elemental analysis for C$_{27}$H$_{43}$N$_7$O$_5$·4HCl·2H$_2$O.

|  | C | H | N | Cl |
|---|---|---|---|---|
| Calculated (%) | 44.57 | 7.07 | 13.48 | 19.49 |
| Found (%) | 45.01 | 7.11 | 13.29 | 19.16 |

EXAMPLE 25

Production of 2″-N-tryptophyl-KA-6606I (A) KA-6606II (215 mg) was reacted and worked up in the same way as in Example 24, (A) to give 316 mg of 1,2′,6′-tris-N-benzyloxycarbonyl-2″-N-(N-benzyloxycarbonyl-L-tryptophyl)-KA-6606I as a colorless solid.

Specific rotation: $[\alpha]_D^{20} +32°$ (c3, CHCl$_3$).

IR value: $\nu_{max}^{CHCl_3}$ cm$^{-1}$ 1635 (amide I).

$^1$H-NMR value: $\delta_{CDCl_3}^{TMS}$ ppm 1.07 (3H, br.t, C—CH$_3$), 2.80, 2.96 (total 3H, s, N—CH$_3$, rotational isomer), 3.25, 3.29 (total 3H, s, O—CH$_3$).

Elemental analysis for C$_{60}$H$_{69}$N$_7$O$_{14}$:

|  | C | H | N |
|---|---|---|---|
| Calculated (%) | 64.79 | 6.25 | 8.82 |
| Found (%) | 65.01 | 6.50 | 8.47 |

(B) The N-protected compound obtained in (A) above (316 mg) was reacted and worked up in the same way as in Example 3, (B) to give 189 mg of the hydrochloride of the desired compound as a colorless solid having the following structural formula.

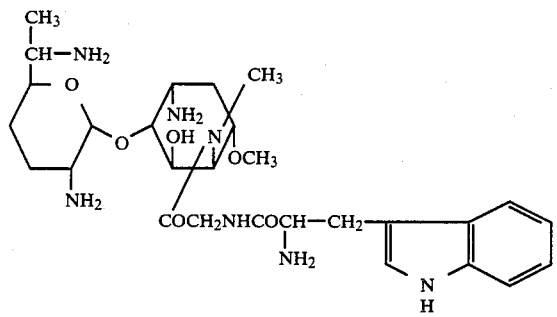

Specific rotation: $[\alpha]_D^{21} +100°$ (c1.04, H$_2$O).

$^1$H-NMR value: $\delta_{D_2O}^{TMS}$ ppm 1.36 (3H, d, J=7.0 Hz, C—CH$_3$), 3.09 (3H, s, N—CH$_3$), 3.46 (3H, s, O—CH$_3$), 5.47 (1H, d, J=3.3 Hz, H-1′), 7.18–7.70 (5H, m, aromatic H).

Elemental analysis for C$_{28}$H$_{45}$N$_7$O$_6$·4HCl·H$_2$O:

|  | C | H | N | Cl |
|---|---|---|---|---|
| Calculated (%) | 45.47 | 6.95 | 13.26 | 19.17 |
| Found (%) | 45.93 | 7.13 | 13.01 | 19.57 |

EXAMPLE 26

Production of 2″-N-L-isoleucyl-5-de-O-methyl-KA-6606I (A) In the same way as in Example 1, (A), 284 mg of 1,2′,6′-tris-N-benzyloxycarbonyl-5-de-O-methyl-KA-6606I obtained in Referential Example 1 and 133 mg of the N-hydroxysuccinimide ester of N-benzyloxycarbonyl-L-isoleucine were reacted, and the reaction produt was purified by silica gel column chromatography [solvent: chloroform/methanol (98:2)] to give 194 mg of 1,2′,6′-tris-N-benzyloxycarbonyl-2″-N-(N-benzyloxycarbonyl-L-isoleucyl)-5-de-O-methyl-KA-6606I as a colorless solid.

Specific rotation: $[\alpha]_D^{22} +33°$ (c5, CHCl$_3$).

IR value: $\nu_{max}^{CHCl_3}$ cm$^{-1}$ 1635 (amide I).

$^1$H-NMR value: $\delta_{CDCl_3}^{TMS}$ ppm 0.85 (3H, t, J=7.5Hz, —CH(CH$_3$)—CH$_2$—CH$_3$), 0.87 (3H, d, J=7.5Hz, —CH(CH$_3$)—CH$_2$—CH$_3$), 1.02 (3H, d, J=7Hz, —CH(NHZ)—CH$_3$) at 6′, 2.88, 3.04 (total 3H, s, N—CH$_3$, rotational isomer).

Elemental analysis for C$_{54}$H$_{68}$N$_6$O$_{14}$:

|  | C | H | N |
|---|---|---|---|
| Calculated (%) | 63.27 | 6.69 | 8.20 |
| Found (%) | 63.04 | 6.96 | 7.92 |

(B) The N-protected compound obtained in (A) above (194 mg) was reacted and worked up in the same way as in Example 3, (B) to give 119 mg of the hydrochloride of the desired compound as a colorless solid having the following structural formula.

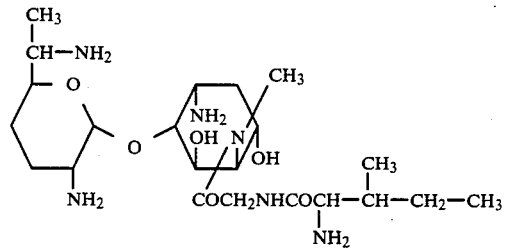

Specific rotation: $[\alpha]_D^{22} +92°$ (c1.03, H$_2$O).

$^1$H-NMR value: $\delta_{D_2O}^{TMS}$ ppm 0.97 (3H, t, J=7.5Hz, —CH(CH$_3$)—CH$_2$—CH$_3$), 1.06 (3H, d, J=7Hz, —CH(CH$_3$)—CH$_2$—CH$_3$), 1.35 (3H, d, J=6.8Hz, —CH(NHZ)—CH$_3$) at 6′, 3.19 (3H, s, N—CH$_3$), 5.51 (1H, d, J=3.5Hz, H-1′).

Elemental analysis for C$_{22}$H$_{44}$N$_6$O$_6$·4HCl·2H$_2$O:

|  | C | H | N | Cl |
|---|---|---|---|---|
| Calculated (%) | 39.41 | 7.82 | 12.53 | 21.15 |
| Found (%) | 39.80 | 8.12 | 12.44 | 21.48 |

EXAMPLE 27

Production of 2''-N-L-histidyl-5-de-O-methyl-KA-6606I (A) In the same way as in Example 1, (A), 402 mg of 1,2',6'-tris-N-benzyloxycarbonyl-5-de-O-methyl-KA-6606I and 270 mg of the N-hydroxysuccinimide ester of 1,N-bisbenzyloxycarbonyl-L-histidine were reacted, and the reaction product was purified by silica gel column chromatography [solvent: chloroform/methanol (10:1)] to give 194 mg of 1,2',6'-tris-N-benzyloxycarbonyl-2''-N-(N-benzyloxycarbonyl-L-histidyl)-5-de-O-methyl-KA-6606I as a colorless solid.

Specific rotation: $[\alpha]_D^{22} + 34°$ (c2,CHCl$_3$).
IR value: $\nu_{max}^{CHCl_3}$ cm$^{-1}$ 1631 (amide I).
$^1$H-NMR value: $\delta_{CDCl_3}^{TMS}$ ppm 1.01 (3H, br.d, J=6 Hz, C—CH$_3$), 2.83, 2.98 (total 3H, s, N—CH$_3$, rotational isomer).

Elemental analysis for C$_{54}$H$_{64}$N$_8$O$_{14}$:

|  | C | H | N |
|---|---|---|---|
| Calculated (%) | 61.82 | 6.15 | 10.68 |
| Found (%) | 62.31 | 6.22 | 10.39 |

(B) The N-protected compound obtained in (A) above (194 mg) was reacted and worked up in the same way as in Example 3, (B) to give 123 mg of the hydrochloride of the desired compound as a colorelss solid having the following structural formula.

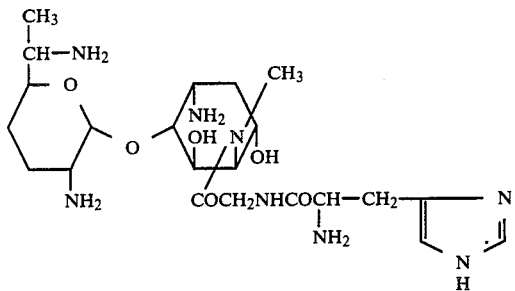

Specific rotation: $[\alpha]_D^{23} + 95°$ (c1.03, H$_2$O).
$^1$H-NMR value: $\delta_{D_2O}^{TMS}$ ppm 1.36 (3H, d, J=7 Hz, C—CH$_3$), 3.19 (3H, s, N—CH$_3$), 5.51 (1H, d, J=3.5 Hz, H-1'), 7.53, 8.76 (each 1H, s, imidazole).

Elemental analysis for C$_{22}$H$_{40}$N$_8$O$_6$.5HCl.2H$_2$O:

|  | C | H | N | Cl |
|---|---|---|---|---|
| Calculated (%) | 36.15 | 6.76 | 15.33 | 24.25 |
| Found (%) | 36.56 | 6.68 | 15.15 | 24.62 |

EXAMPLE 28

Production of 2''-N-D-tryptophyl-5-de-O-methyl-KA-6606I (A) 497 mg of 1,2',6'-tris-N-benzyloxycarbonyl-5-de-O-methyl-KA-6606II and 540 mg of the N-hydroxysuccinimide ester of N-benzyloxycarbonyl-D-tryptophylglycine were dissolved in 20 ml of dioxane, and 0.3 ml of triethylamine was added. The mixture was left to stand overnight at 37° C. The reaction mixture was concentrated to dryness. The residue was dissolved in chloroform, washed with water, dried, and then concentrated to dryness. The residue was dissolved in 10 ml of methanol. Then, 3 ml of a 30% ethanol solution of methylamine was added. The mixture was stirred at room temperature for 1 hour, and concentrated to dryness. The residue was purified by silica gel column chromatography [solvent: chloroform/methanol (97:3)] to give 427 mg of 1,2',6'-tris-N-benzyloxycarbonyl-2''-N-(N-benzyloxycarbonyl-D-tryptophyl-5-de-O-methyl-KA-6606I as a colorless solid.

Specific rotation: $[\alpha]_D^{19} + 36°$ (c1.5, CHCl$_3$).
IR value: $\nu_{max}^{CHCl_3}$ cm$^{-1}$ 1635 (amide I).
$^1$H-NMR value: $\delta_{CDCl_3}^{TMS}$ ppm 0.99 (3H, br.d, C—CH$_3$), 2.80, 2.92 (total 3H, s, N—CH$_3$, rotational isomer).

Elemental analysis for C$_{59}$H$_{67}$N$_7$O$_{14}$:

|  | C | H | N |
|---|---|---|---|
| Calculated (%) | 64.53 | 6.15 | 8.93 |
| Found (%) | 64.41 | 6.42 | 8.69 |

(B) The N-protected compound obtained in (A) above (427 mg) was reacted and worked up in the same way as in Example 3, (B) to give 261 mg of the hydrochloride of the desired compound as a colorless solid.

Specific rotation: $[\alpha]_D^{19} + 35°$ (c1.02, H$_2$O).
$^1$H-NMR value: $\delta_{D_2O}^{TMS}$ ppm 1.36 (3H, d, J=7 Hz, C—CH$_3$), 3.12 (3H, s, N—CH$_3$), 5.49 (1H, d, J=3.5 Hz, H-1'), 7.16-7.72 (5H, m, aromatic H).

Elemental analysis for C$_{27}$H$_{43}$N$_7$O$_6$.4HCl.2H$_2$O:

|  | C | H | N | Cl |
|---|---|---|---|---|
| Calculated (%) | 43.61 | 6.91 | 13.19 | 19.07 |
| Found (%) | 44.05 | 7.13 | 12.94 | 18.94 |

EXAMPLE 29

Production of 4-N-(L-glutamyl-beta-alanyl)-5-de-O-methyl-KA-6606II (A) In the same way as in Example 28, (A), 722 mg of 1,2',6'-tris-N-benzyloxycarbonyl-5-de-O-methyl-KA-6606II and 420 mg of the N-hydroxysuccinimide ester of gamma-O-benzyl-N-benzyloxycarbonyl-L-glutamyl-beta-alanine were reacted, and the reaction product was purified by silica gel column chromatography [solvent: chloroform/methanol (50:1)] to give 606 mg of 1,2',6'-tris-N-benzyloxycarbonyl-4-N-[(gamma-O-benzyl-N-benzyloxycarbonyl-L-glutamyl)-beta-alanyl]-5-de-O-methyl-KA-6606II as a colorless solid.

Specific rotation: $[\alpha]_D^{24} + 28°$ (c1, CHCl$_3$).
$^1$H-NMR value: $\delta_{CDCl_3}^{TMS}$ ppm 1.04 (3H, d, J=6.5 Hz, C—CH$_3$), 2.90 (3H, s, N—CH$_3$).

Elemental analysis for C$_{61}$H$_{72}$N$_6$O$_{16}$:

|  | C | H | N |
|---|---|---|---|
| Calculated (%) | 63.97 | 6.34 | 7.34 |
| Found (%) | 63.22 | 6.35 | 7.25 |

(B) The N,O-protected Compound obtained in (A) above (606 mg) was reacted and worked up in the same way as in Example 3, (B) to give 337 mg of the hydrochloride of the desired compound as a colorless solid having the following structural formula.

[Structure diagram with CH₃, CH-NH₂, O, NH₂, OH, N, OH, CH₃, NH₂, COCH₂CH₂NHCOCHCH₂CH₂COOH, NH₂]

Specific rotation: $[\alpha]_D^{22} + 78°$ (c1, H₂O).

¹H-NMR value: $\delta_{D_2O}^{TMS}$ ppm 1.37 (3H, d, J=6.5 Hz, C—CH₃), 2.57 (2H, t, J=7.5 Hz, C—CH₂—COOH), 2.79 (2H, t, J=6.5 Hz, —NCOCH₂CH₂N), 3.18 (3H, s, N—CH₃), 5.53 (1H, d, J=3 Hz, H-1').

EXAMPLE 30

Production of 4-N-(L-tryptophyl-beta-alanyl)-5-de-O-methyl-KA-6606II (A) In the same way as in Example 28, (A), 830 mg of 1,2',6'-tris-N-benzyloxycarbonyl-5-de-O-methyl-KA-6606II and 500 mg of the N-hydroxysuccinimide ester of N-benzyloxycarbonyl-L-tryptophyl-beta-alanine were reacted, and the reaction product was purified by silica gel column chromatography [solvent: chloroform/methanol (40:1)] to give 670 mg of 1,2',6'-tris-N-benzyloxycarbonyl-4-N-[(N-benzyloxycarbonyl-L-tryptophyl)-beta-alanyl]-5-de-O-methyl-KA-6606II as a colorless solid.

Specific rotation: $[\alpha]_D^{22} + 33°$ (c1, CHCl₃).

¹H-NMR value: $\delta_{CDCl_3}^{TMS}$ ppm 1.02 (3H, d, J=6.5 Hz, C—CH₃), 2.87 (3H, s, N—CH₃).

Elemental analysis for C₆₀H₆₉N₇O₁₄:

|  | C | H | N |
|---|---|---|---|
| Calculated (%) | 64.79 | 6.25 | 8.82 |
| Found (%) | 64.27 | 6.33 | 8.56 |

(B) The N-protected compound obtained in (A) above (645 mg) was reacted and worked up in the same way as in Example 3, (B) to give 360 mg of the hydrochloride of the desired compound as a colorless solid having the following structural formula.

[Structure diagram with CH₃, CH-NH₂, O, CH₃, NH₂, OH, N, OH, NH₂, COCH₂CH₂NHCOCH—CH₂-indole, NH₂]

Specific rotation: $[\alpha]_D^{22} + 91°$ (c1, H₂O).

¹H-NMR value: $\delta_{D_2O}^{TMS}$ ppm 1.34 (3H, d, J=7 Hz, C—CH₃), 3.02 (3H, s, N—CH₃), 5.47 (1H, d, J=3.3 Hz, H-1').

7.35 (1H, s, [pyrrole fragment with H and N]).

Elemental analysis for C₂₈H₄₅N₇O₆·4HCl·2H₂O:

|  | C | H | N | Cl |
|---|---|---|---|---|
| Calculated (%) | 44.39 | 7.05 | 12.94 | 18.72 |
| Found (%) | 43.56 | 7.22 | 12.51 | 19.04 |

What is claimed is:

1. An aminoglycoside compound represented by the following formula (1)

[Structure diagram showing formula (1) with R₁, CH—NH—R₂, O, NH₂, CH₃, OH, N, R₃, NH₂, CO(CH₂)ₙ—NH—A·H]

wherein
R₁ and R₂ are different from each other and each represents a hydrogen atom or a methyl group,
R₃ represents a hydrogen atom, a hydroxyl group or a methoxy group,
A represents a residue of a C₂-C₁₁ amino acid or a residue of a dipeptide composed of two said amino acids which are identical or different, and
n represents 1 or 2;
or its acid addition salt.

2. The aminoglycoside compound or its acid addition salt according to claim 1 wherein A represents a residue of a natural alpha-amino acid having 2 to 11 carbon atoms, or a residue of a dipeptide composed of two such amino acids which are identical or different.

3. The aminoglycoside compound or its acid addition salt according to claim 1 wherein A is a residue of an amino acid selected from the group consisting of glycine, alanine, beta-alanine, valine, leucine, isoleucine, serine, threonine, aspartic acid, glutamic acid, asparagine, glutamine, cystine, cysteine, lysine, beta-lysine, ornithine, arginine, histidine, phenylalanine, tyrosine, tryptophan, proline and methionine, or a residue of a dipeptide composed of two such amino acids which are identical or different.

* * * * *